United States Patent
Hu et al.

(10) Patent No.: US 9,749,593 B2
(45) Date of Patent: Aug. 29, 2017

(54) OPTICAL FIBER STRUCTURE, ILLUMINATION UNIT, ENDOSCOPE, AND A METHOD OF MANUFACTURING AN OPTICAL FIBER STRUCTURE

(71) Applicant: FUJIKURA LTD., Koto-ku, Tokyo (JP)

(72) Inventors: Wei-Zhi Hu, Sakura (JP); Kenichi Nakatate, Sakura (JP); Hitoe Iikura, Sakura (JP); Hideo Shiratani, Sakura (JP)

(73) Assignee: FUJIKURA LTD., Tokyo (JP)

( * ) Notice: Subject to any disclaimer, the term of this patent is extended or adjusted under 35 U.S.C. 154(b) by 471 days.

(21) Appl. No.: 14/176,638

(22) Filed: Feb. 10, 2014

(65) Prior Publication Data
US 2014/0152789 A1   Jun. 5, 2014

Related U.S. Application Data

(63) Continuation of application No. PCT/JP2012/070537, filed on Aug. 10, 2012.

(30) Foreign Application Priority Data

Aug. 12, 2011 (JP) .................. 2011-176736
Aug. 12, 2011 (JP) .................. 2011-176737
Aug. 12, 2011 (JP) .................. 2011-176738

(51) Int. Cl.
*H04N 7/18* (2006.01)
*G02B 23/24* (2006.01)
(Continued)

(52) U.S. Cl.
CPC ............. *H04N 7/18* (2013.01); *A61B 1/0011* (2013.01); *A61B 1/0017* (2013.01);
(Continued)

(58) Field of Classification Search
CPC ...... H04N 7/18; G02B 6/4415; G02B 6/0005; G02B 6/4479; G02B 6/449;
(Continued)

(56) References Cited

U.S. PATENT DOCUMENTS 3,826,852 A    7/1974 Levaco et al.
4,173,392 A   11/1979 Ekinaka et al.
(Continued)

FOREIGN PATENT DOCUMENTS

GB    2336000    *  9/1998
GB    2336000 A  * 10/1999
(Continued)

OTHER PUBLICATIONS

Machine translation for JP 06-186445A filed Feb. 10, 2014.
(Continued)

*Primary Examiner* — Tung Vo
*Assistant Examiner* — Zaihan Jiang
(74) *Attorney, Agent, or Firm* — Sughrue Mion, PLLC

(57) ABSTRACT

An optical fiber structure according to the present application includes a cylindrical resin body, and a plurality of circumferential arrays of optical fiber bare wires disposed within the resin body and extending along a longitudinal direction of the resin body. The resin body includes a linear slit provided at a location intermediate the length of the resin body. The linear slit extends from an outer surface to an inner bore of the resin body and extending substantially parallel to the bare wires.

37 Claims, 15 Drawing Sheets

(51) Int. Cl.
    *A61B 1/00*     (2006.01)
    *F21V 8/00*     (2006.01)
    *G02B 6/06*     (2006.01)
    *B29D 11/00*     (2006.01)
    *G02B 6/44*     (2006.01)
    *A61B 1/06*     (2006.01)
    *A61B 1/07*     (2006.01)

(52) U.S. Cl.
    CPC ........ *A61B 1/00167* (2013.01); *A61B 1/0607* (2013.01); *A61B 1/0623* (2013.01); *A61B 1/07* (2013.01); *B29D 11/00663* (2013.01); *G02B 6/0005* (2013.01); *G02B 6/0008* (2013.01); *G02B 6/06* (2013.01); *G02B 6/449* (2013.01); *G02B 6/4415* (2013.01); *G02B 6/4479* (2013.01); *G02B 23/2469* (2013.01)

(58) Field of Classification Search
    CPC .............. G02B 23/2469; G02B 6/0008; B29D 11/00663; A61B 1/07; A61B 1/0017
    USPC ............ 348/65; 385/100; 362/556; 264/1.28
    See application file for complete search history.

(56) References Cited

U.S. PATENT DOCUMENTS

| | | | | |
|---|---|---|---|---|
| 6,252,722 | B1* | 6/2001 | Kittaka | G02B 23/243 359/654 |
| 2003/0026919 | A1* | 2/2003 | Kojima | C03C 25/12 427/558 |
| 2006/0289189 | A1* | 12/2006 | Aisenbrey | H05B 3/56 174/36 |
| 2008/0019647 | A1* | 1/2008 | Sato | G02B 6/4403 385/112 |
| 2009/0092364 | A1* | 4/2009 | Johnston | A61B 1/00096 385/117 |

FOREIGN PATENT DOCUMENTS

| | | |
|---|---|---|
| JP | 48-49970 A | 7/1973 |
| JP | 56-158305 A | 12/1981 |
| JP | 60-39604 A | 3/1985 |
| JP | 61-261554 A | 11/1986 |
| JP | 5-288935 A | 11/1993 |
| JP | 5-346509 A | 12/1993 |
| JP | 6-186445 A | 7/1994 |
| JP | 2001-324628 A | 11/2001 |
| JP | 2002-245821 A | 8/2002 |
| WO | 2009116969 A1 | 9/2009 |

OTHER PUBLICATIONS

Machine translation for JP 05-346509A filed Feb. 10, 2014.
Machine translation for JP 2001-324628A filed Feb. 10, 2014.
Machine translation for JP 2002-245821A filed Feb. 10, 2014.
Communication dated Jan. 28, 2014 from the Japanese Patent Office in counterpart application No. 2011-176737.
Communication dated Feb. 4, 2014 from the Japanese Patent Office in counterpart application No. 2011-176736.
Communication dated Mar. 20, 2015 from the European Patent Office in counterpart application No. 12823584.3.
International Search Report for PCT/JP2012/070537 dated Oct. 30, 2012.
Office Action for JP Application No. 2011-176736 dated Nov. 26, 2013.
Office Action for JP Application No. 2011-176737 dated Nov. 26, 2013.
Office Action for JP Application No. 2011-176738 dated Nov. 26, 2013.

* cited by examiner

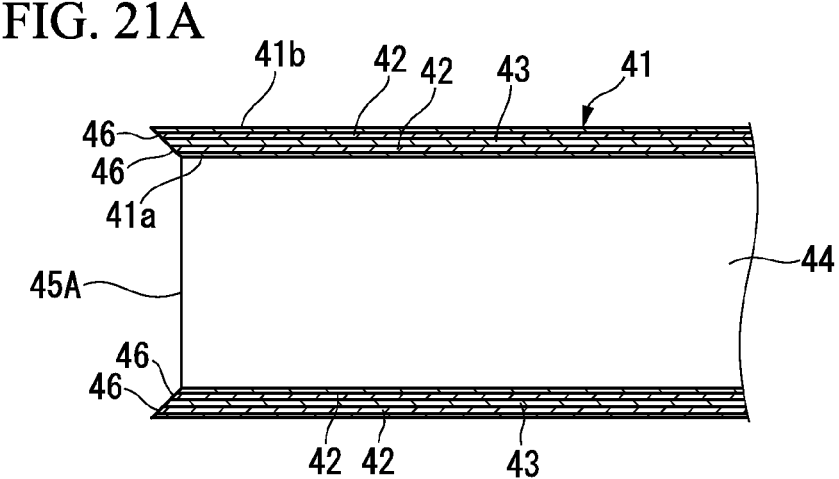
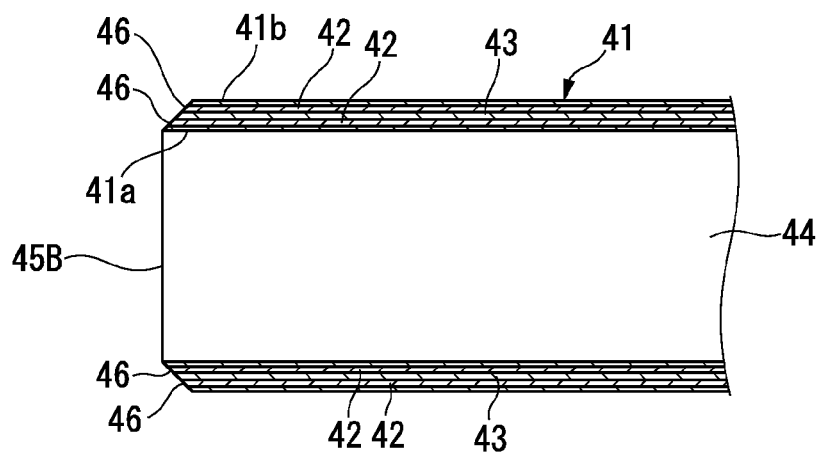
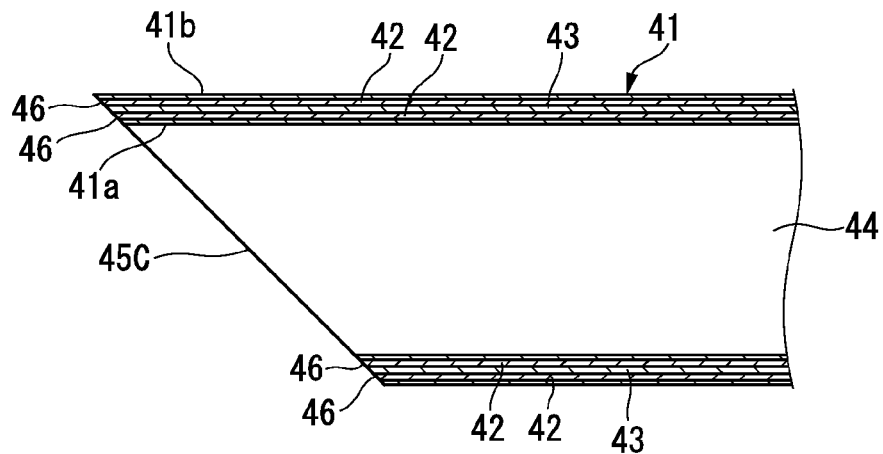

OPTICAL FIBER STRUCTURE, ILLUMINATION UNIT, ENDOSCOPE, AND A METHOD OF MANUFACTURING AN OPTICAL FIBER STRUCTURE

CROSS REFERENCE TO RELATED APPLICATIONS

This application is a continuation application based on a PCT Patent Application No. PCT/JP2012/070537, filed Aug. 10, 2012, whose priority is claimed on Japanese Patent Applications No. 2011-176736, No. 2011-176737 and No. 2011-176738 filed Aug. 12, 2011, the entire contents of which are hereby incorporated by reference.

BACKGROUND OF THE INVENTION

Field of the Invention

The present invention relates to an optical fiber structure suitable for used in an illumination unit, an endoscope and the like, an illumination unit and an endoscope both having the optical fiber structure, and a method of manufacturing an optical fiber structure.

Description of the Related Art

Conventionally, using an optical fiber made of multicomponent glasses (multicomponent fiber) as a light guide to transmit illumination light in an endoscope and other illumination units is known.

Also, Japanese Unexamined Patent Application, First Publication No. H5-288935 discloses a cylindrical optical fiber structure (hereinafter, simply referred to as the "structure") where a plurality of circumferential arrays of bare optical fibers are coated with a light transmittable resin so that light is illuminated from its side with a lesser chance of uneven light distribution.

A conventional multicomponent fiber light guide is composed of a bundle of multicomponent fibers; therefore, it is relatively easy to change the shape of the bundle when the bundle is bent or split so as to incorporate the light guide into an endoscope. However, such a conventional multicomponent fiber light guide is relatively expensive to manufacture since the multicomponent fibers need to be bundled.

The structure as described in Japanese Unexamined Patent Application, First Publication No. H5-288935 is inexpensive to manufacture since the structure can be made in its entirety by extrusion. The structure is, however, intended for side illumination (light is emitted from the cylindrical outer surface), and Japanese Unexamined Patent Application, First Publication No. H5-288935 is silent on the use of the structure as a light guide with axial illumination.

In view of the foregoing problems, the present invention provides an optical fiber structure serving as an economical light guide suitable for use in an endoscope, an illumination unit and an endoscope both having the optical fiber structure, and a method of manufacturing an optical fiber structure.

SUMMARY OF THE INVENTION

In order to solve the aforementioned problems, the present invention provides the following structures.

In the first aspect, an optical fiber structure includes a cylindrical resin body, and a plurality of circumferential arrays of optical fiber bare wires disposed within the cylindrical resin body and extending along a longitudinal direction of the resin body. The resin body includes a linear slit provided at a location intermediate the length of the resin body. The linear slit extends from an outer surface to an inner bore of the resin body and extends substantially parallel to the bare wires.

In the second aspect, the resin body includes a plurality of the slits arranged at regular intervals in a circumferential direction, and elongated portions each sandwiched between the two adjacent slits in the resin body. The elongated portions are overlapped so that the resin body has a narrower outer circumference.

In the third aspect, the slits are provided in the resin body at opposed positions as viewed from a longitudinal direction of the resin body, and elongated portions each sandwiched between the slits are deformed to a flat shape as viewed from a longitudinal direction of the resin body.

In the fourth aspect, an illumination unit includes the optical fiber structure of any one of the first to third aspects, and a light source arranged at one end of the optical fiber structure.

In the fifth aspect, an endoscope includes the optical fiber structure of any one of the first to third aspects, and an image transmission unit which transmits an image of a target portion under inspection is disposed in the inner bore of the resin body so as to face an end portion of the optical fiber structure.

In the sixth aspect, in the endoscope of the fifth aspect, the image transmission unit transmits the image captured by an imaging sensor.

In the seventh aspect, in the endoscope of the fifth aspect, the image transmission unit is an image fiber.

In the eighth aspect, in the endoscope of the fifth aspect, the image transmission unit is inserted through the slit provided at a location intermediate the length of the resin body.

In a ninth aspect, an optical fiber structure includes a ring fiber having a cylindrical resin body, a plurality of circumferential arrays of optical fiber bare wires disposed within the cylindrical resin body and extending in a longitudinal direction of the resin body. The ring fiber includes a processed end formed by cutting at least one longitudinal end of the ring fiber along a longitudinal direction of the bare wires and overlapping separated portions in a circumferential direction of the ring fiber so that the processed end is narrower than a cylindrical section of the ring fiber.

In the tenth aspect, in the optical fiber structure of the ninth aspect, the processed end is inserted into a fitting which tightens the processed end.

In the eleventh aspect, in the optical fiber structure of the ninth or tenth aspect, the processed end is formed by twisting the end of the ring fiber.

In the twelfth aspect, in the optical fiber structure of any one of the ninth to eleventh aspects, a light entry projection is formed at the tip of the processed end, the light entry projection includes a curved and convexed surface and formed by transparent adhesive with a refractive index lower than that of the bare wires.

In the thirteenth aspect, in the optical fiber structure of any one of the ninth to twelfth aspects, the processed end includes a plurality of discrete portions dividedly formed during the cutting of the end of the ring fiber and collected together.

In the fourteenth aspect, in the optical fiber structure of the tenth aspect, the fitting includes a taper hole.

In the fifteenth aspect, a method of manufacturing an optical fiber structure includes a ring fiber having a cylindrical resin body, and a plurality of circumferential arrays of optical fiber bare wires disposed within the cylindrical resin body and extending along a longitudinal direction of the resin body. The method includes cutting at least one longitudinal end of the ring fiber in along a longitudinal direction of the bare wires, overlapping separated portions in a circumferential direction of the ring fiber, and forming a processed end so as to be narrower than a cylindrical section of the ring fiber.

In the sixteenth aspect, the method of manufacturing an optical fiber structure of the fifteenth aspect further includes inserting the end subjected to the cutting process of the ring fiber into a fitting which tightens the end.

In the seventeenth aspect, the method of manufacturing an optical fiber structure of the fifteenth or sixteenth aspect further includes twisting the end subjected to the cutting process of the ring fiber.

In the eighteenth aspect, the method of manufacturing an optical fiber structure of any one of the fifteenth to seventeenth aspects includes forming a light entry projection including a curved and convexed surface at a tip of the processed end by using transparent adhesive with a refractive index lower than that of the bare wires.

In the nineteenth aspect, the method of manufacturing an optical fiber structure of any one of the fifteenth to eighteenth aspects includes collecting a plurality of discrete portions as dividedly formed during the cutting of the end of the ring fiber.

In the twentieth aspect, an optical fiber structure includes a ring fiber having a cylindrical resin body, a plurality of circumferential arrays of optical fiber bare wires disposed within the cylindrical resin body and extending in a longitudinal direction of the resin body. The ring fiber includes a plurality of discrete portions formed by cutting at least one longitudinal end of the ring fiber along a longitudinal direction of the bare wires. The discrete portions are separated away from each other.

In the twenty-first aspect, a method of manufacturing an optical fiber structure includes a ring fiber having a cylindrical resin body, a plurality of circumferential arrays of optical fiber bare wires is disposed within the cylindrical resin body and extends in a longitudinal direction of the resin body. The method includes cutting at least one longitudinal end of the ring fiber along a longitudinal direction of the bare wires and forming a plurality of discrete portions, and separating the discrete portions away from each other.

In the twenty-second aspect, in an illumination unit includes the optical fiber structure of the twentieth aspect, a plurality of light sources arranged at the input end of the optical fiber structure so that the light sources correspond to the discrete portions.

In the twenty-third aspect, an optical fiber structure includes a cylindrical resin body, and a plurality of circumferential arrays of optical fiber bare wires disposed within the cylindrical resin body and extending in a longitudinal direction of the resin body. The resin body includes at least one longitudinal end, and the bare wires include inclined end faces at the end of the resin body.

In the twenty-fourth aspect, in the optical fiber structure of the twenty-third aspect, at the end, the end faces of the bare wires are inclined together with an end face of the resin body around the end faces of the bare wires.

In the twenty-fifth aspect, in the optical fiber structure of the twenty-third aspect, the output end includes an outer periphery and an inner periphery. The outer periphery is shaped to project beyond the inner periphery along the entire circumference of the output end.

In the twenty-sixth aspect, in the optical fiber structure of the twenty-third aspect, the output end includes an outer periphery and an inner periphery. The inner periphery is shaped to project beyond the outer periphery along the entire circumference of the output end.

In the twenty-seventh aspect, in the optical fiber structure of the twenty-fourth aspect, the output end in its entirety is inclined along a single plane.

In the twenty-eighth aspect, in an illumination unit includes the optical fiber structure of any one of the ninth to fourteenth aspects and the twenty-third to twenty-seventh aspects, a light source is arranged at the input end of the optical fiber structure.

In the twenty-ninth aspect, an endoscope includes the optical fiber structure of any one of the nineteenth to fourteenth aspects, the twentieth aspect, and the twenty-third to twenty-seventh aspects, an image transmission unit is disposed within the optical fiber structure that transmits an image of a target portion under inspection that opposes the output end faces.

In the thirtieth aspect, in the endoscope of the twenty-ninth aspect, an imaging sensor is provided at a distal end of the image transmission unit In the thirty-first aspect, in the endoscope of the twenty-ninth aspect, the image transmission unit is an image fiber.

According to the ninth aspect, the optical fiber structure enhances the efficiency of inputting light to the optical fiber structure from the light source. It is therefore possible to readily increase the amount of outgoing light from one end of the optical fiber structure at a location longitudinally opposite to the other end where light from the light source enters.

In the ring fiber used to manufacture the optical fiber structure, a plurality of circumferential arrays of optical fiber bare wires are disposed within the cylindrical resin body and extend in a longitudinal direction of the resin body. This construction enables the optical fiber structure to be readily manufactured at a low cost, for example, by drawing. The use of the ring fiber also brings about a decrease in the cost of the optical fiber structure.

According to the twenty-third aspect, the shape of the output end is changed in such a manner that outgoing light can be collected at the center, can be diffused in an outward direction, or can be applied to a lateral direction substantially transverse to the longitudinal direction of the optical fiber structure.

According to the present invention, there is provided an inexpensive light guide suitable for use in an endoscope.

BRIEF DESCRIPTION OF DRAWINGS

FIG. 21A is a longitudinal sectional view of the first example of the optical fiber structure according to the third embodiment of the present invention, with the shape of an output end of the optical fiber structure shown.

FIG. 21B is a longitudinal sectional view of the second example of the optical fiber structure according to the third embodiment of the present invention, with the shape of an output end of the optical fiber structure shown.

FIG. 21C is a longitudinal sectional view of a third example of the optical fiber structure according to the third embodiment of the present invention, with the shape of an output end of the optical fiber structure shown.

DETAILED DESCRIPTION OF THE PREFERRED EMBODIMENTS

First Embodiment

An endoscope according to the first embodiment of the present invention will hereinafter be described with reference to FIGS. 1 to 7.

Figure 1:
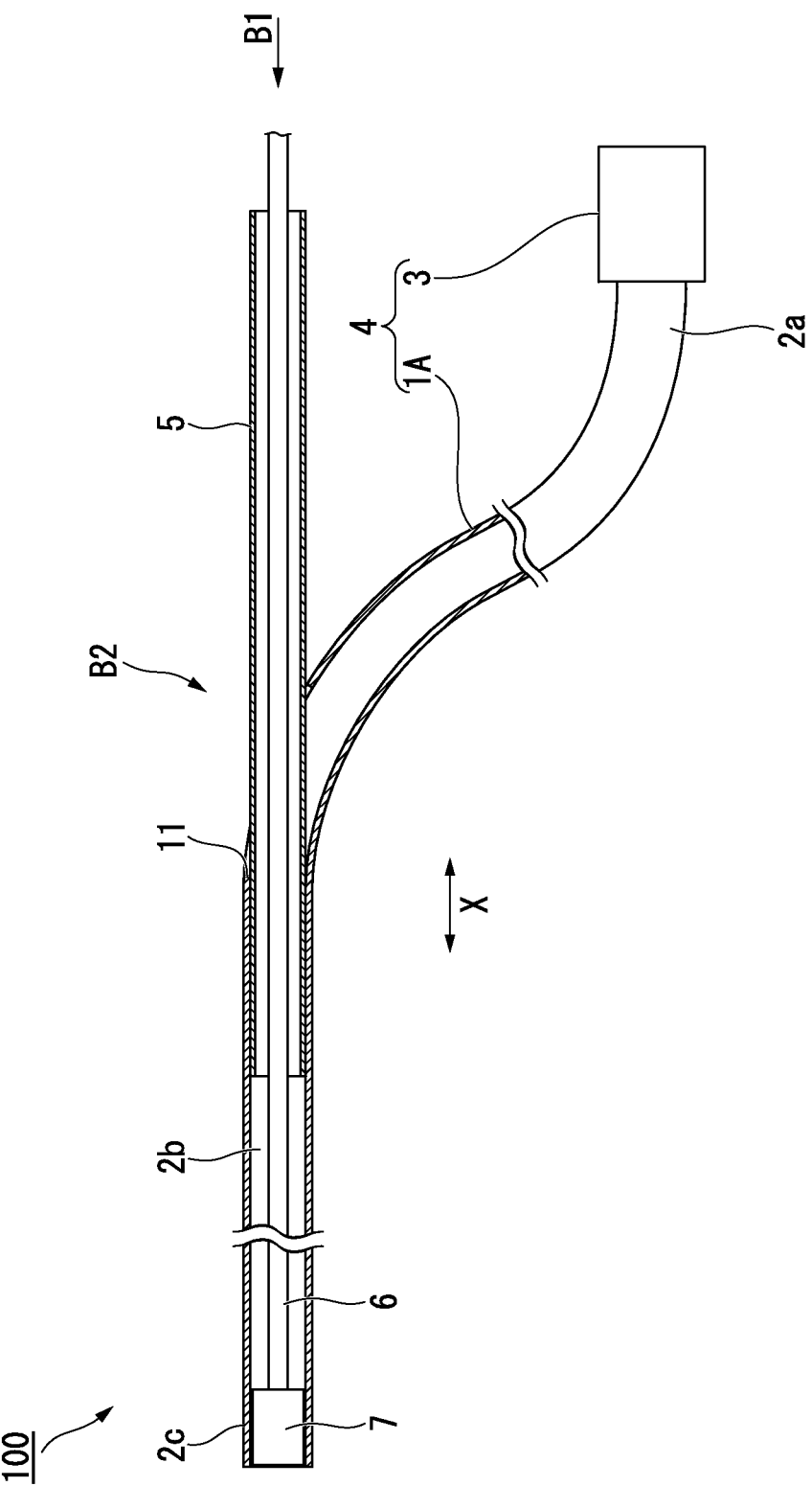
FIG. 1 is a side view, partly broken away, of an endoscope according to the first embodiment of the present invention.
Figure 2:
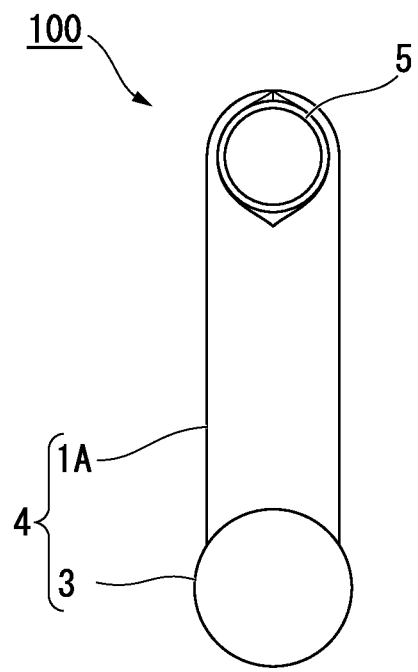
FIG. 2 is a view of the endoscope as viewed in a direction shown by arrow B1 in FIG. 1.

As shown in FIGS. 1 and 2, an endoscope 100 includes an illumination unit 4 having a cylindrical structure 1A of the present invention and a light source 3 arranged at an input end (one end) 2a of the structure 1A, a tubular body 5 having a distal end inserted into the structure 1A, an image fiber (image transmission unit) 6 disposed in an inner bore 2b of the structure 1A, and an objective lens 7 disposed at a distal end of the image fiber 6.

Figure 3:
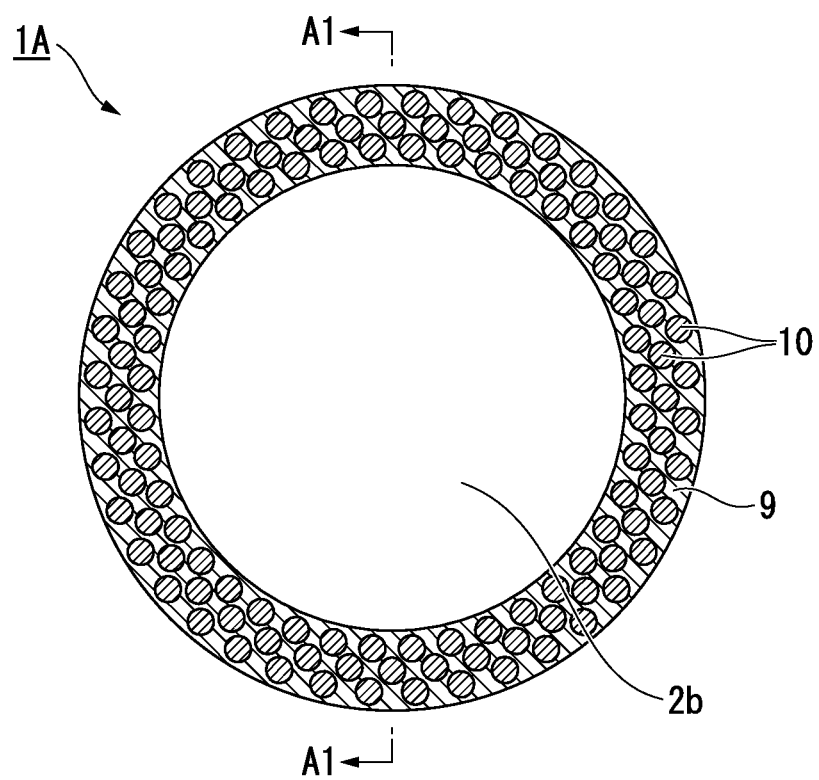
FIG. 3 is a cross-sectional view of one example of a section perpendicular to a longitudinal direction of a structure used in the endoscope.
Figure 4:
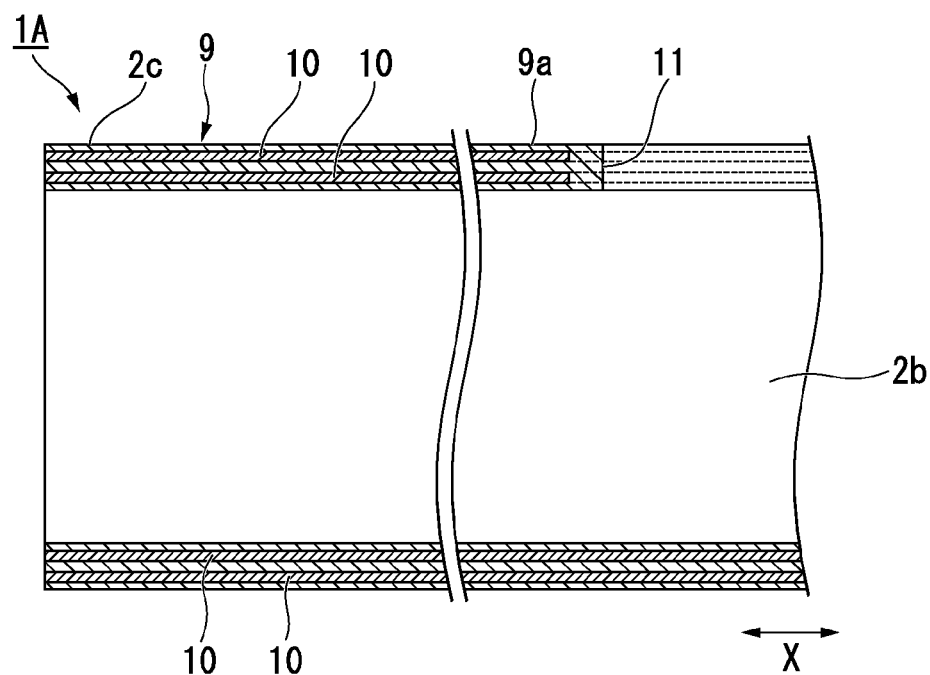
FIG. 4 is a sectional view taken on the line A1-A1 in FIG. 3.

As shown in FIGS. 3 and 4, the structure 1A of the present invention includes a cylindrical resin body 9 and a plurality of circumferential arrays of optical fiber bare wires 10 disposed within the resin body 9 and extending in the longitudinal direction X of the resin body 9. These optical fiber bare wires 10 disposed within the cylindrical resin body 9 will hereinafter be referred to as a "ring fiber".

The structure 1A has a ring-shaped section, as viewed in a direction transverse to the longitudinal direction X. The inner bore 2b is centrally formed in the ring-shaped structure 1A and extends in the longitudinal direction X.

The plurality of bare wires 10 disposed within the resin body 9 extends in the longitudinal direction X.

The bare wires 10 are composed of plastic optical fibers (POF) each having a core surrounded by a resin sheath (both not shown). The resin sheath has a refractive index lower than that of the core. Each of the bare wires 10 utilizes the refractive index difference between the core and the sheath and serves as an optical waveguide. The core and the sheath are both made of plastic capable of transmitting light through the structure 1A. Illustratively, a few to a few hundreds of bare wires 10 are disposed within the resin body 9.

The plastic material of which the core of each of the bare wires 10 is made is not limited to the specific plastic material. Any of those core plastic materials used in a conventional plastic optical fiber may be used. For example, plastic materials for the bare wires can include methyl methacrylate homopolymer (polymethyl methacrylate; PMMA), methyl methacrylate-acrylic acid ether copolymer, methyl methacrylate-styrene copolymer, polycarbonate, a styrene-based resin, or the like.

The plastic material of which the resin sheath of each of the bare wires 10 is made is not limited to the specific plastic material. Any of those sheath plastic materials used in a conventional plastic optical fiber may be used. For example, the sheath plastic materials can include vinylidene fluoride-tetrafluoroethylene copolymer, vinylidene fluoride-hexafluoropropene copolymer, vinylidene fluoride-tetrafluoroethylene-hexafluoropropene copolymer, vinylidene fluoride-trifluoroethylene-hexafluoroacetone copolymer, a fluoroalkyl methacrylate resin, ethylene vinyl acetate copolymer, or the like.

The resins of which the resin body 9 is made can include polyethylene, ethylene vinyl acetate copolymer, ethylene-ethylene acrylate copolymer, polyvinyl chloride, thermoplastic polyurethane, an elastomer made from styrene butadiene block copolymer or a double bond between the copolymers, most of which is hydrogenated, vinylidene fluoride-hexafluoropropene copolymer, vinylidene fluoride-hexafluoropropene-tetrafluoroethylene copolymer, vinylidene fluoride-chlorotrifluoroethylene copolymer silicone resins, and the like.

The bare wires 10 and the resin body 9 made of the materials such as the above-described plastic are deformable without breakage and crack when the structure 1A is bent to a predetermined radius of curvature. That is, the bare wires 10 and the resin body 9 are made of a substantially soft material.

As shown in FIGS. 1 to 4, a slit 11 is formed in the resin body 9 of the structure 1A at a location intermediate its length along the longitudinal direction X. The slit 11 extends along a straight line and substantially parallel to the bare wires 10. The slit 11 is made by cutting the resin body 9. The slit 11 extends from an outer surface 9a of the resin body 9 to the inner bore 2b.

As shown in FIG. 1, the light source 3 includes, for example, LEDs and emits light toward an input end 2a of the structure 1A.

Optical coupling between the input end 2a of the structure 1A and the light source 3 is not limited to the specific form. The input end 2a may be processed in such a manner that light is inputted to the bare wires 10 from the light source 3. Alternatively, the input end 2a may not be processed as far as light is inputted to the bare wires 10 from the light source 3.

The tubular body 5 is made, but not limited to, of stainless steel. The tubular body 5 may also be made of aluminum, resin, or the like.

Figure 5:
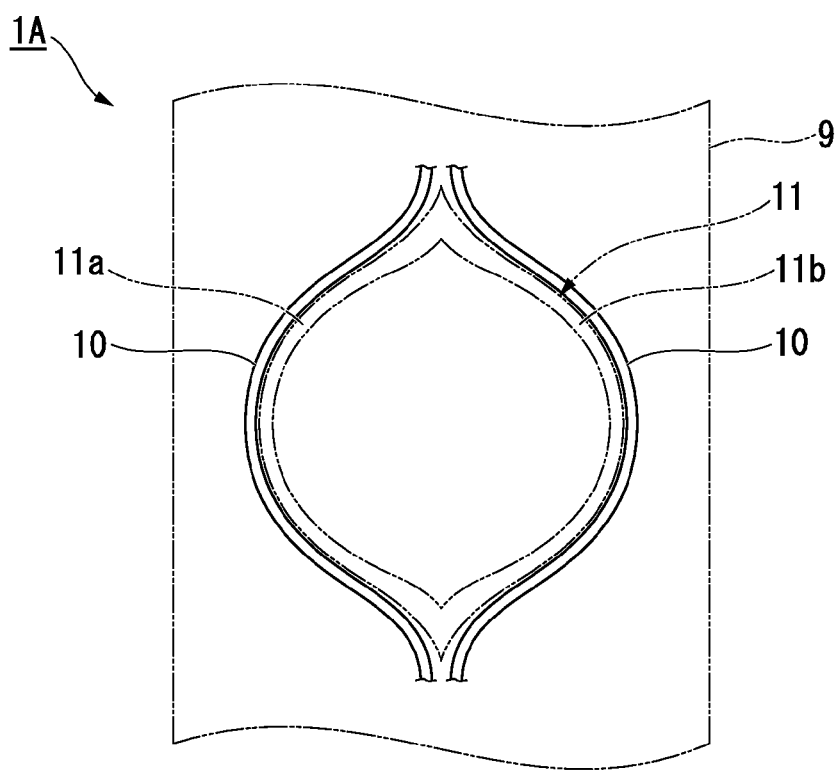
FIG. 5 is a view of the endoscope as viewed in a direction shown by arrow B2 in FIG. 1.

FIG. 5 is a view of the structure as seen in the direction of the arrow B2 in FIG. 1. For purposes of illustration, only the structure 1A is shown in FIG. 5, with the resin body 9 shown by double-dotted line.

As shown in FIGS. 1 to 5, the structure 1A is bent at a region corresponding to the slit 11. At this time, the slit 11 is outwardly bent from the structure 1A. Also, opposite inner walls 11a, 11b of the slit 11 are centrally deformed so that the inner walls 11a, 11b are moved away from each other.

A portion of the bare wires 10 located adjacent to the inner wall 11a is bent along the inner wall 11a without breakage. Likewise, a portion of the bare wires 10 located adjacent to the inner wall 11b is bent along the inner wall 11b without breakage.

The distal end of the tubular body 5 is inserted into the structure 1A through the slit 11 and extends to a position in between the output end (distal end) 2c of the structure 1A and the slit 11.

Insertion of the distal end of the tubular body 5 through the slit 11 holds the shape of the structure 1A, as bent in a region corresponding to the slit 11, and also, the shape of the inner walls 11a, 11b of the slit 11, as centrally deformed and separated away from each other.

In the present embodiment, the tubular body 5 is inserted through the slit 11 of the structure 1A. Alternatively, the slit 11 and the tubular body 5 may be bonded together by using such as an adhesive.

The objective lens 7 is disposed in the inner bore 2b and located at the output end 2c of the structure 1A.

The objective lens 7 collects light as reflected back from a target portion under inspection against which the output end 2c of the structure 1A is positioned and provides a corresponding optical image. The image fiber 6 transmits the optical image to the proximal end of the structure.

Reference will now be made to a method of manufacturing the structure 1A according to the present embodiment and incorporated into the endoscope 1 constructed as described above.

A method of manufacturing the structure 1A includes a forming step of arranging a plurality of bare wires 10 within the resin body 9 and a cutting step of defining the slit 11 in the structure 1A.

First, in the forming step, the bare wire 10 is made beforehand by providing a sheath on the outer surface of a core. The plurality of bare wires 10 and resin as a raw material for the resin body 9 are supplied to a coating die in an extruder, not shown. The coating die includes orifices corresponding to the bare wires 10. The plurality of bare wires 10 are placed along a predetermined reference axis and arranged around the reference axis.

When the bare wires 10 and molten resin are extruded from the coating die, gas is centrally supplied from the coating die to define a bore of the desired shape in the center of the molten resin.

After the plurality of bare wires 10 and the molten resin are extruded along the reference axis, cooling takes place to form the cylindrical resin body 9 within which the plurality of bare wires 10 are placed.

Next, in the cutting step, the resin body 9 is cut along a straight line parallel to the bear wires 10 so that the resulting slit 11 extends from the outer surface 9a of the resin body to the inner bore 2b. The worker can readily define the slit 11 by the use of a knife as the structure 1A is made of plastic.

Some of the bare wires 10 may accidentally be cut while the slit 11 is provided in the structure 1A. It will not pose a problem if the number of the bare wires 10 as cut is negligible as compared to the total number of the bare wires 10.

Reference will next be made to one example of how the endoscope 1 constructed as described above is used.

When light is emitted from the light source 3, the light then enters the input end 2a of the structure 1A. The light is transmitted to the output end 2c while being guided by the bare wires 10. The light illuminates in a direction forwardly of the structure 1A. The user inserts the distal end of the structure 1A into a narrow body cavity while at the same time, viewing before the structure 1A by means of the image fiber 6. When the distal end of the structure 1A approaches a target portion under inspection, light is emitted from the structure 1A. The light is then reflected back from the target portion under inspection. The reflected light is collected by the objective lens 7 and the image fiber 6 so as to allow observation of the target portion in inspection.

As described above, in the endoscope 1 of the present embodiment, the structure 1A includes the slit 11, and the slit 11 enables the image fiber 6 and the like to be readily inserted into the inner bore 2b of the structure 1A. Also, the slit 11 is formed so as to extend parallel to the bare wires 10.

This arrangement prevents cutting of the bare wires 10 and thus, suppresses a decrease in the amount of light as transmitted through the bare wires 10.

The bare wires 10 and the resin body 9 of the structure 1A are made of substantially soft material, as mentioned above. This allows the bare wires 10 and the resin body 9 to be bent along the inner walls 11a, 11b without breakage when the structure 1A is bent in a region corresponding to the slit 11, and the opposite inner walls 11a, 11b of the slit 11 are centrally deformed and separated away from each other. As such, a sufficient space can be provided between the inner walls 11a, 11b to receive the image fiber 6 or the like.

The tubular body 5 is inserted into the structure 1A through the slit 11. This arrangement prevents damages to the slit 11 due to for example, rubbing which may occur when the image fiber 6 or the like is inserted through the slit 11.

The light source 3 is provided at the input end 2a of the structure 1A. The structure 1A and the light source 3 form the illumination unit 4. This construction enables light from the light source 3 to be transmitted through each of the bare wires 10 and then, emitted out of the output end 2c. Therefore, the structure 1A of the present embodiment is suitable for use in the endoscope 1.

Additionally, the image fiber 6 is positioned within the inner bore 2b of the structure 1A. The image fiber 6 is capable of transmitting light from its distal to proximal end.

The image fiber 6 acts as an image transmission unit. Thus, transmission of light from its distal to proximal end of the image fiber 6 can be made with a simple construction.

The structure 1A can be manufactured at a low cost, by extruding the entire structure 1A.

In the present embodiment, where insertion of the image fiber 6 or the like through the slit 11 is required only a small number of times, the tubular body 5 may be omitted because there is a less chance of the slit 11 suffering from damages.

Although a preferred embodiment of the present invention has been described, the present invention is not limited to the foregoing examples. Various modifications and changes may be made without departing from the spirit of the present invention.

In the embodiment, the structure 1A is used in an exposed condition. Alternatively, the structure 1A may be surrounded by a separate jacket, tube or the like.

Also, in the embodiment, the image fiber 6 is used as an image transmission unit. Alternatively, an electrically conductive wire may be used as an image transmission unit. In this case, an imaging sensor (imaging unit) such as a CCD is connected to the distal end of the electrically conductive wire. Images are captured by the imaging sensor and converted to an electrical signal which is transmitted through the electrically conductive wire. This alternative arrangement can make the outer diameter of the image transmission unit and the structure 1A smaller.

In the embodiment, one slit 11 is provided in the circumferential direction of the structure. No limitation is imposed on the number of the slit 11. A plurality of slits 11 may be provided in the circumferential direction of the structure. Also, in the embodiment, the slit 11 is provided at a location intermediate the length of the resin body along the longitudinal direction X. No limitation is imposed on where the slit 11 is provided, unless the slit 11 extends through the whole length of the resin body 9 in the longitudinal direction X. For example, the slit 11 may be provided at a portion of the resin body 9 other than the distal end of the resin body 9. Specifically, the slit 11 may extend from the middle portion of the resin body 9 to the proximal end of the resin body 9.

Figure 6:
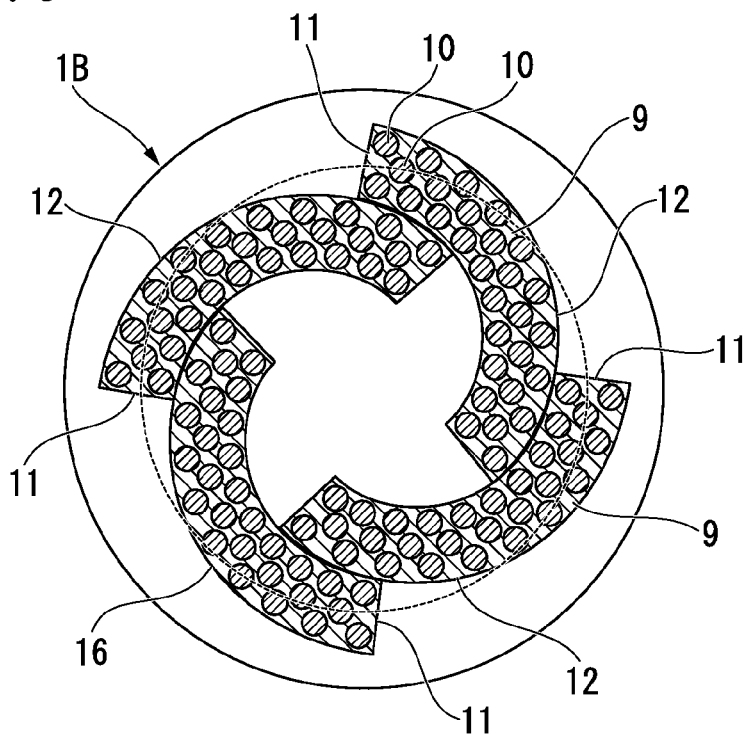
FIG. 6 is a sectional view showing the shape of another example of the structure used in the first embodiment of the present invention.

In a structure 1B as shown in FIG. 6, a plurality of slits 11 are provided in the resin body 9 in a circumferentially spaced relationship. In the present modified example, four slits 11 are provided in the resin body 9 at regular intervals in a circumferential direction. No limitation is imposed on the number of the slits 11 to be provided in the resin body 9. Two or more slits 11 may be provided therein.

Two adjacent slits 11 of the resin body 9 collectively form an elongated portion 12 circumferentially sandwiched therebetween, as part of the structure 1B. In the present modified example, four elongated portions 12 are provided.

The elongated portions 12 adjacent in the circumference direction are overlapped with each other so as to narrow the outer circumference of a portion of the resin body 9 where the slits 11 are provided in the longitudinal direction X.

The structure 1B thus constructed can be more easily inserted into a narrower body cavity or the like.

Figure 7:
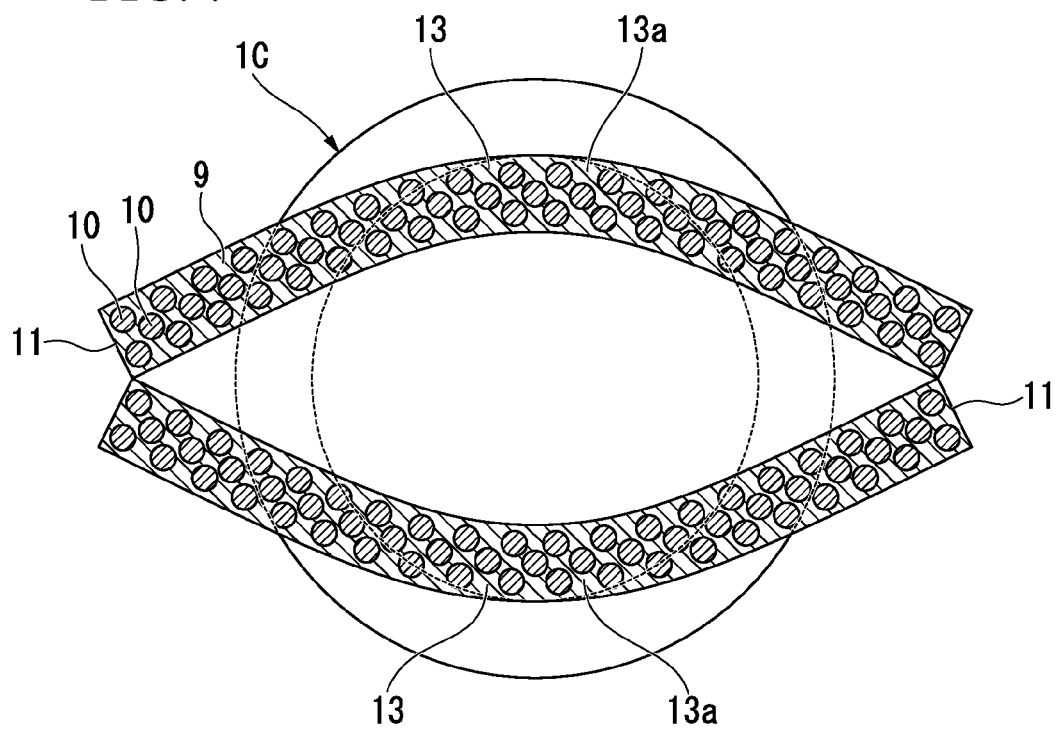
FIG. 7 is a sectional view showing the shape of a different example of the structure used in the first embodiment of the present invention.

In the embodiment, in a structure 1C as shown in FIG. 7, slits 11 are each provided in the resin body 9 in an opposed position as viewed in the longitudinal direction X. Two elongated portions 13 are sandwiched between these slits 11. The two elongated portions 13 are made flat as viewed in the longitudinal direction X. Specifically, each of the elongated portions 13 has a middle portion 13a at a location intermediate the width of the resin body 9. The two middle portions 13a of the elongated portions 13 are moved toward each other so as to make the structure flat.

The structure 1C thus constructed can be easily inserted into an elongated portion such as a channel, since the structure 1C made flat.

When the structure is sufficiently soft, for example, the structure may be made flat at a portion where the slit 11 is not formed.

In the embodiment, the resin body 9 has a cylindrical shape. However, the shape of the resin body is not limited to a cylindrical shape. The resin body may have an ellipsoidal or polygonal shape, as viewed in the longitudinal direction X Second Embodiment An endoscope according to the second embodiment of the present invention will now be described with reference to FIGS. 21A to 25.

Figure 8A:
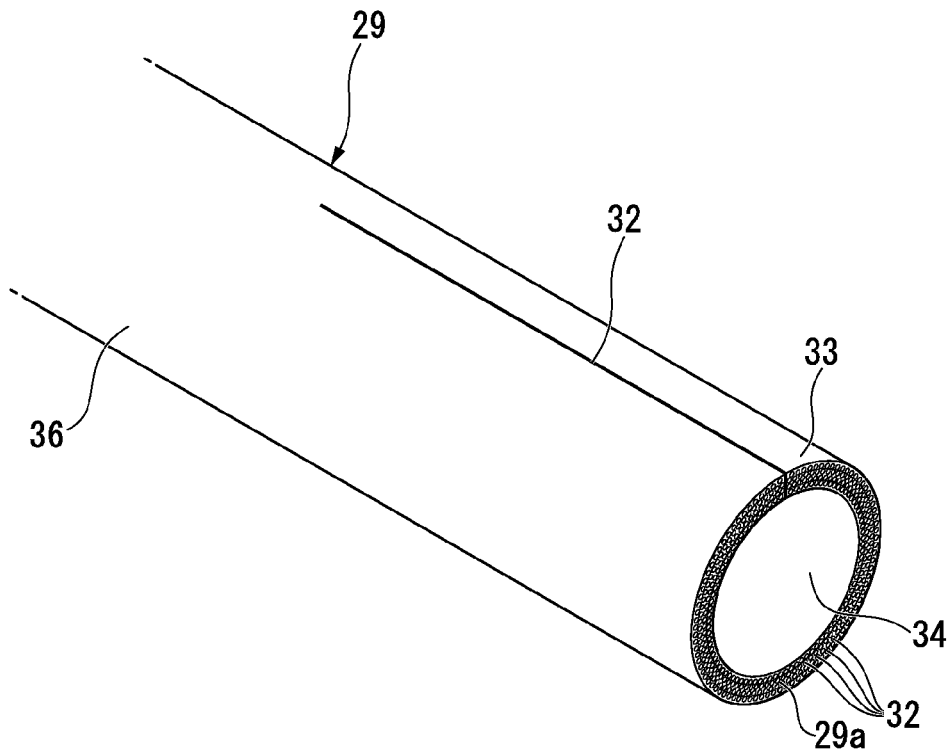
FIG. 8A illustrates the second embodiment of the present invention and is a perspective view showing the manner in which one end of a ring fiber is cut in a longitudinal direction of bare wires.
Figure 8B:
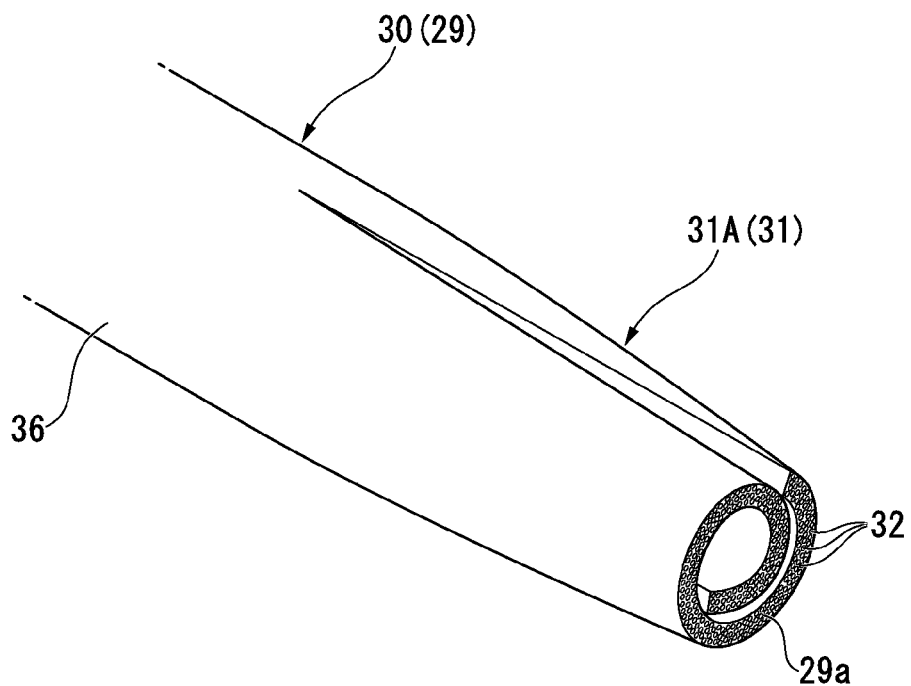
FIG. 8B illustrates the second embodiment of the present invention and is a perspective view showing the construction of a processed end of the ring fiber.
Figure 9A:
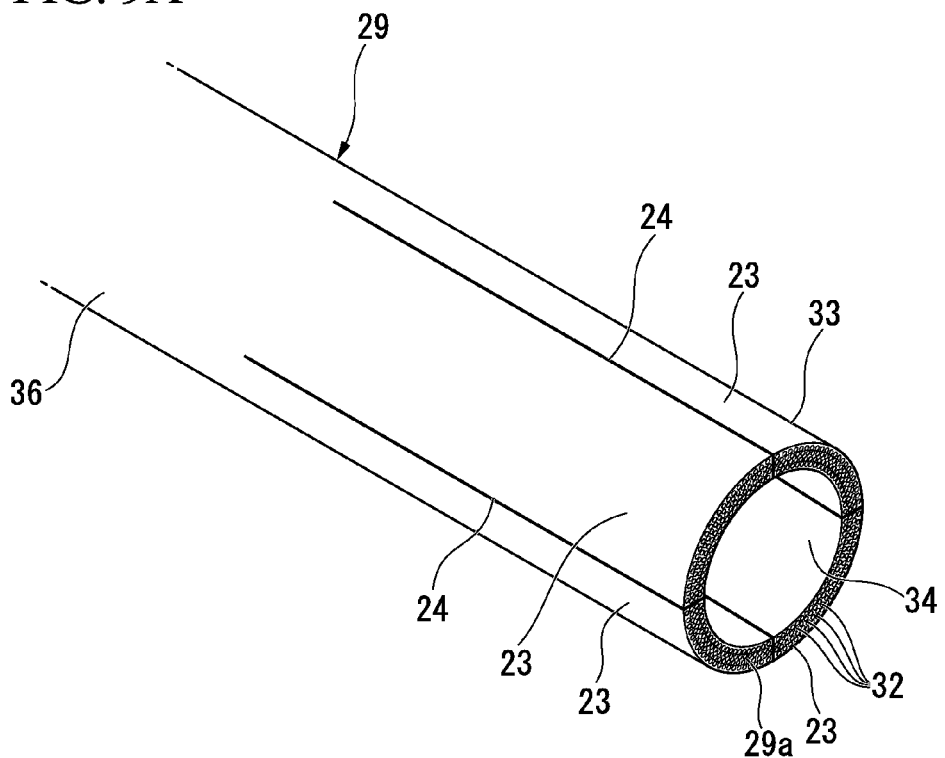
FIG. 9A illustrates the second embodiment of the present invention and is a perspective view showing the manner in which one end of the ring fiber is cut in a longitudinal direction of the bare wires.
Figure 9B:
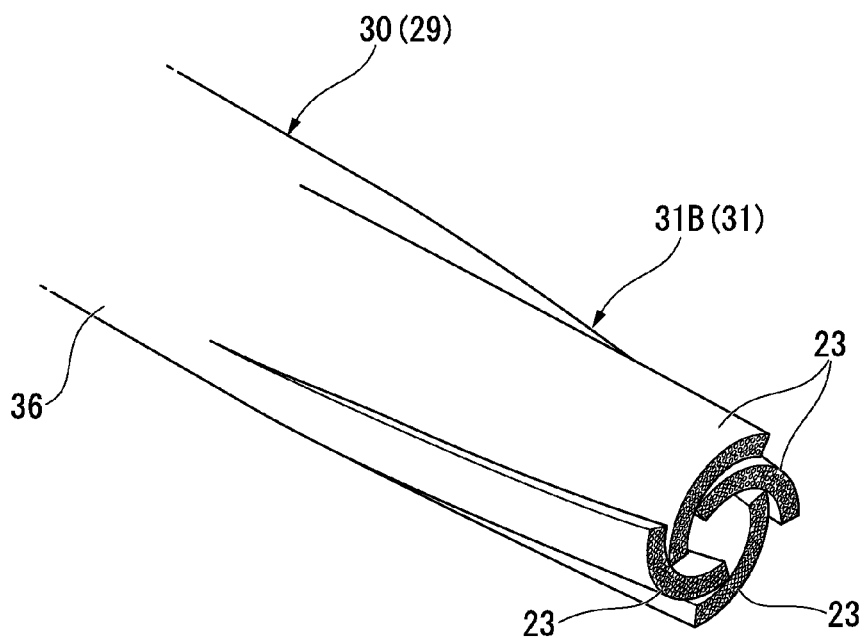
FIG. 9B illustrates the second embodiment of the present invention and is a perspective view showing the construction of a processed end of the ring fiber.

FIGS. 8B and 9B show the first and second examples of an optical fiber structure 30 made according to the second embodiment of the present invention, and illustrate the shape of an input end (processed end 31 as will later be described) of the optical fiber structure 30.

Figure 10:
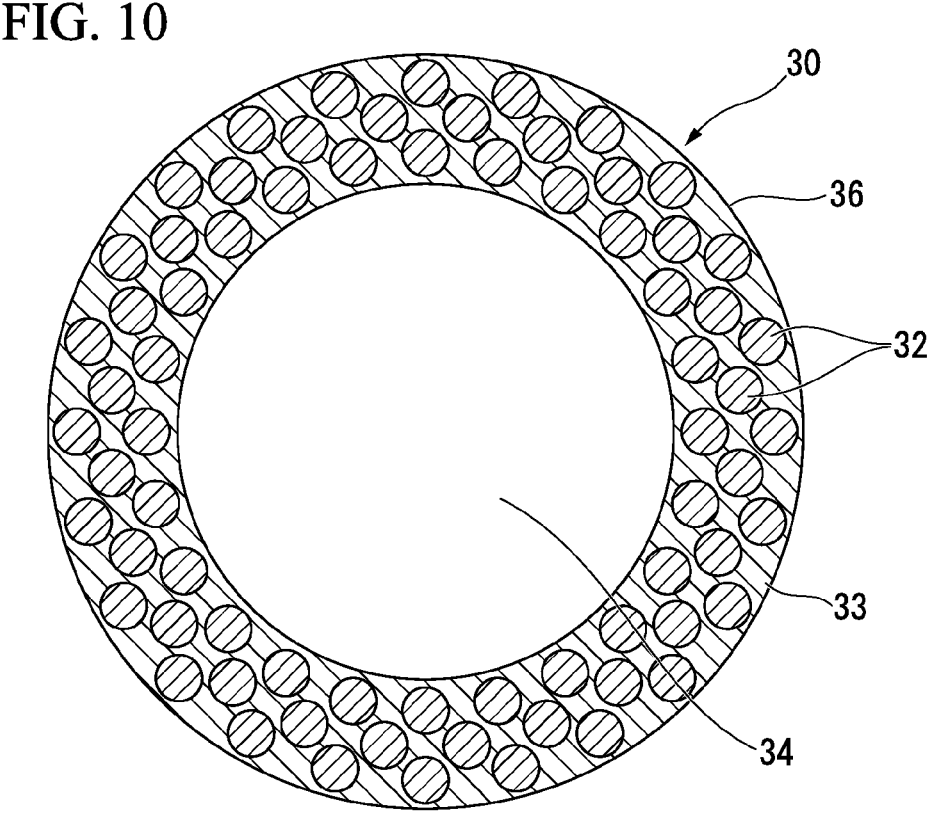
FIG. 10 is a cross-sectional view showing one example of a section perpendicular to a longitudinal direction of a cylindrical section of the optical fiber structure of the present invention.
Figure 11:
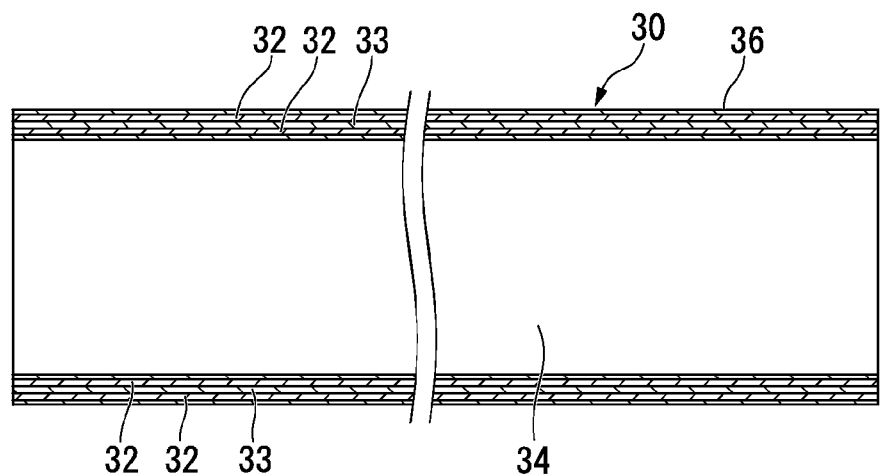
FIG. 11 is a longitudinal sectional view showing one example of the ring fiber before one end of the ring fiber is processed.

As shown in FIGS. 10 and 11, the optical fiber structure 30 is composed of a ring fiber 29 where a plurality of circumferential arrays of the bare wires 32 of an optical fiber along with a longitudinal direction of a resin body 33 are disposed within a cylindrical resin body 33. In this optical fiber structure 30, one longitudinal end of the ring fiber 29 is narrower than the cylindrical portion of the ring fiber 29. The narrowed end is hereinafter referred to as "processed end 31".

In the ring fiber 29, a section which is vertical to the longitudinal direction thereof has a ring-shaped section. The resin body 33 has a hollow portion 34. The plurality of bare wires 32 is disposed within the resin body 33. These bare wires 32 extend in the longitudinal direction (or lateral direction in FIGS. 8A and 8B) of the ring fiber 29. The bare wires 32 are each composed of a plastic optical fiber (POF) with a core surrounded by a resin sheath having a refractive index lower than that of the core. Each of the bare wires 32 utilizes the refractive index difference between the core and the resin sheath and serves as an optical waveguide. The core and the resin sheath are both made of plastic capable of transmitting light through the optical fiber structure 30.

The plastic material of which the core of the bear wire 32 is made is the same as the plastic material used in the first embodiment.

The plastic material of which the resin sheath of the bear wire 32 is made is the same as the plastic material used in the first embodiment.

The resin of which the resin body 33 is made is the same as the resin used in the first embodiment.

The ring fiber 29 can be economically made, for example, by extrusion. The ring fiber 29 is flexible to the extent that the user can easily bend the ring fiber 29 by hand.

Also, the ring fiber 29 can easily be cut with a knife. For example, one longitudinal end of the ring fiber 29 can be cut along the length of the bare wires so as to split the ring fiber 29 into a plurality of sections.

Figure 13:
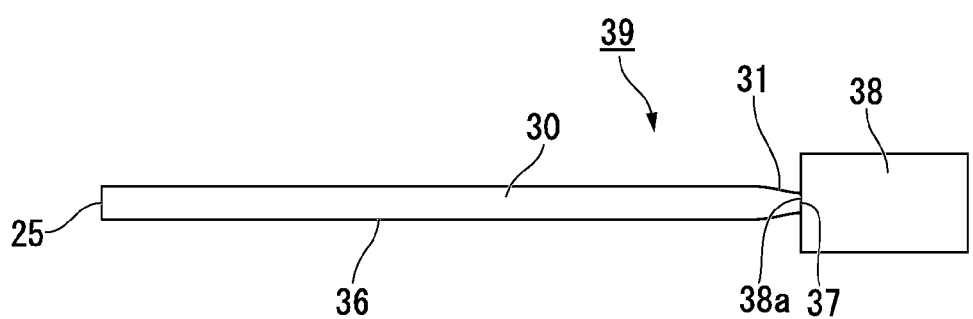
FIG. 13 is a schematic view showing the manner in which a light source (illumination unit) is arranged at an input end of the optical fiber structure.

As shown in FIG. 13, the optical fiber structure 30 has one longitudinal or input end 37 and the other longitudinal or output end 25 opposite the input end 37. The bare wires 32 and the resin body 33 extend from the input end 37 to the output end 25 along the length of the optical fiber structure 30. The hollow portion 34 also extends along the length of the optical fiber structure 30 and is open at the opposite ends (that is, the input end 37 and the output end 25).

A light source 38 is arranged at the input end 37 of the optical fiber structure 30 as shown in FIG. 13 so that light emitted from the light source 38 can be transmitted through each of the bare wires 32 and outputted from the output end 25.

Figure 12:
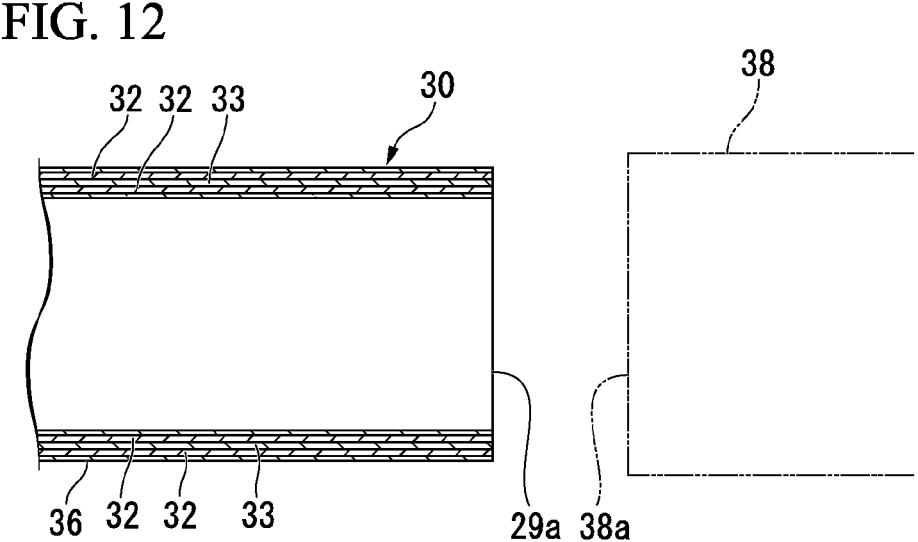
FIG. 12 is a sectional view of one end of the ring fiber shown in FIG. 11.

As shown in FIG. 12, in a conventional plastic optical fiber structure, one end of the cylindrical ring fiber 29 in the longitudinal direction is left unprocessed and used as an input end. When an LED (Light Emitting Diode) is used as the light source 38 to emit light to the optical fiber structure, a central emitting face 38a of the LED is aligned with the central axis of the input end of the optical fiber structure (ring fiber 29) as shown by phantom line in FIG. 12. In this way, light can be uniformly inputted to the optical fiber structure.

In contrast, according to the present invention, at least one longitudinal end, processed end 31, of the optical fiber structure 30 is narrower than a cylindrical portion of the optical fiber structure 30 as shown in FIG. 13. A typical LED has a light emitting profile such that the intensity of light emitted from the outer periphery of the light emitting face is lower than that of light emitted from the center portion of the light emitting face. To this end, the center portion of the light emitting face 38a of the light source (LED) 38 is aligned with the central axis of the processed end 31 where the light source 38 (LED) is arranged at the processed end 31 of the optical fiber structure 30, and the processed end 31 is used as the input end 37 to receive light from the light source 38, as shown in FIG. 13. This arrangement achieves high optical coupling efficiency between the light source 38 and the optical fiber structure.

In contrast to the optical fiber structure with the cylindrical input end as shown in FIG. 12, the optical fiber structure 30 enables the end face of each of the bare wires 32 located at the input end 37 to be placed closer to the axis of light from the light source 38. This arrangement achieves high optical coupling efficiency between the light source 38 and the optical fiber structure. Accordingly, the optical fiber structure 30 can receive a greater amount of light (or achieve high light entry efficiency) from the light source 38 than the optical fiber structure shown in FIG. 12. Also, the optical fiber structure 30 can provide a greater amount of light from the output end than the optical fiber structure shown in FIG. 12.

The LED is a light source which dissipates heat substantially less than incandescent bulbs and the like during light emission. Heat generated by a light source can deform the optical fiber structure, deteriorate the mechanical properties and increase light loss. Therefore, it is preferable to use an LED as the light source 38.

An LED may be used as the light source 38 in all the embodiments of the present invention.

In the optical fiber structure 30 of the present invention, a method of forming the processed end 31 includes cutting one longitudinal end (simply, referred to as "an end" in the present Description) of the ring fiber 29 in the longitudinal direction of the bare wires 32 (a cutting step), and overlapping adjacent portions as separated from each other in the circumferential direction of the ring fiber 29 so that the one end of the ring fiber is narrower than a cylindrical portion 36 of the ring fiber 29 (an end forming step).

The optical fiber structure 30 is manufactured by processing the ring fiber 29 which is easy and economical to manufacture. The optical fiber structure 30 can therefore be manufactured at a low cost.

The shape of the processed end 31 is fixed, for example, by an adhesive. The end forming step includes a step of fixing the shape of the processed end 31.

The overlapped portion is bonded and fixed by an adhesive. The portions where adjacent portions as separated from each other in the circumferential direction of the ring fiber 29 are overlapped, effectively aids in shape fixity and shape stability of the processed end 31.

In FIGS. 8A and 9A, reference numeral 24 denotes a slit provided by cutting one end of the ring fiber 29. In FIGS. 8A and 9A, the slit 24 starts from an end face 29a of the ring fiber 29 and extends along the length of the bare wires 32. Cutting of the end of the ring fiber 29 (cutting step) is a procedure to circumferentially separate the end of the ring fiber 29 into one or a plurality of portions and make the end of the ring fiber 29 discrete. Cutting of the end of the ring fiber 29 along the length of the bare wires 32 reduces the number of the bare wires 32 cut and thus, effectively increases the amount of light emitted out of the output end of the optical fiber structure 30.

The end of the ring fiber 29 is cut, for example, by a knife Laser cutting or any other known techniques which are employed to cut plastic materials may alternatively be used.

As the ring fiber 29 is made of plastic, the ring fiber 29 can readily be cut with a knife As shown in FIGS. 8A and 9A, the processed end 31 (reference numeral 31A is added to the drawings) of the first example is formed by cutting the end of the ring fiber 29 along the length of the bare wires 32, with only one cut in its circumferential direction, and winding the end around the axis (axis of cylindrical section 36) of the ring fiber 29 to form the end with a taper shape (frustoconically wound section) extending from the cylindrical section 36. The shape of the processed end 31A is fixed, for example, with an adhesive. Different portions of the processed end 31A are overlapped with each other in a circumferential direction of the ring fiber 29.

A pair of cut edges is formed when the end of the ring fiber 29 is cut. In the processed end 31A shown in FIG. 8B, one of the two cut edges of the ring fiber 29 is wound inwardly of the other cut edge along approximately one third of the circumference of the ring fiber 29.

In the processed end 31A, one of the cut edges (overlapped portion) of the ring fiber 29 is inserted inwardly of the other cut edge on an end in a circumferential direction (outer winding cut edge) so that the both cut edges are overlapped with each other (overlapped area). It should be noted that in the processed end 31A, the size of the overlapped portion at the end of the ring fiber 20 may vary appropriately.

In the second example shown in FIGS. 9A and 9B, the processed end 31 (reference numeral 31B is added to the drawings) is formed by cutting the end of the ring fiber 29 along the length of the bare wires 32, with a plurality of cuts in its circumferential direction, so as to divide the end into a plurality of (illustratively, four) discrete portions 23 (cutting step), moving the four discrete portions 23 toward each other and fixing the shape of the four discrete portions 23 with an adhesive. The end faces of the bare wires 32 are exposed from the end faces of the discrete portions 23.

The processed end 31B (discrete portion collection end) also extends convergingly from the cylindrical section 36 and has a convergingly tapered shape. In the processed end 31B adjacent discrete portions 23 formed as a result of cutting the end of the ring fiber 29 are overlapped with each other.

The shape of the processed end 31 may be fixed by means other than an adhesive.

For example, after the cutting step, heat may be applied to a plurality of portions of the end or to the entire end of the ring fiber 29 so as to fuse the overlapped portions of the end of the ring fiber 29 together.

Alternatively, after the end of the ring fiber 29 is cut, the cylindrical section 36 of the ring fiber 29 may be snugly fit into a ring-shaped fitting 28 having an inner diameter less than the outer diameter of the cylindrical section 36, so as to fix the shape of the processed end 31. The fitting 28 may have a C-shape as at 28a in FIG. 15. As an alternative, the fitting may be free of circumferential discontinuity.

Figure 14A:
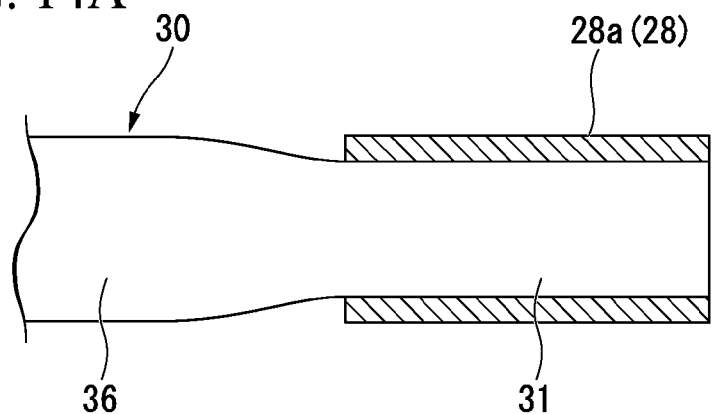
FIG. 14A is a view showing the manner in which the processed end is fit into a fitting.
Figure 14B:
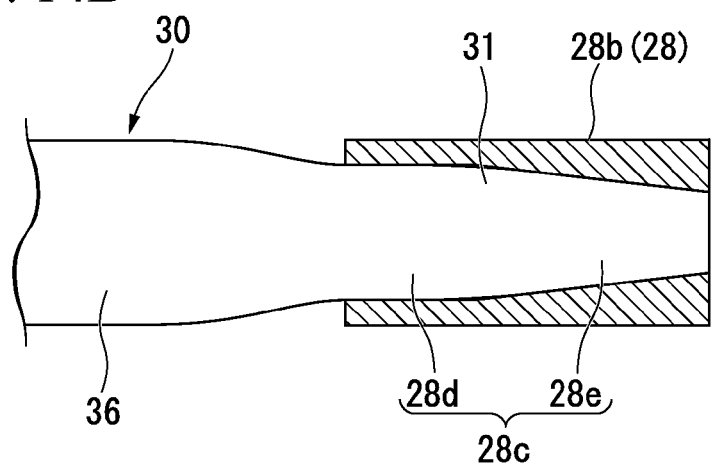
FIG. 14B is a view showing the manner in which the processed end is fit into a fitting.

As shown in FIG. 14A, the fitting 28a has a through-hole 28c. The through-hole 28c has a fixed diameter throughout its length. However, the fitting 28 may have a taper hole as shown in FIG. 14B. In FIG. 14B, the fitting 28 is accompanied by reference numeral 28b.

As shown in FIG. 14B, the fitting 28b has a through-hole 28c. The through-hole 28c includes a straight opening or hole section 28d at its one axial end, and a taper hole section 28e convergingly extending from the straight hole section 28d. The straight hole section 28d has an inner diameter slightly less than the outer diameter of the cylindrical section 36 of the ring fiber 29. After the end of the ring fiber 29 is cut, the end of the ring fiber 29 is snugly fit into the straight hole section 28d of the through hole 28c so as to tighten the end of the ring fiber 29 and thus, fix the shape of the processed end 31.

The fitting 28b with the taper hole may have a C-shape or may be free of circumferential discontinuity. Also, the fitting 28b may have a taper hole throughout its length. As an alternative, the fitting 28b may have a hole with an inner diameter equal to or slightly greater than the outer diameter of the cylindrical section 36 of the ring fiber 29. This hole has no effect on the tightening of the processed end 31.

In the examples shown in FIGS. 14A and 14B, the slit end of the ring fiber 29 is snugly fit into and tightened by the fitting 28 (fitting step). As such, the end of the ring fiber 29 is held in position within the fitting 28. The fitting 28 serves to fix the shape of the end 31 and also, functions to retain the fixed shape When the slit end of the ring fiber 29 is snugly fit into the fitting 28 before the shape of the end of the ring fiber 29 is fixed, the fitting 28 tightens the end of the ring fiber 29 so that the processed end 31 can have a desired shape. The fitting 28 also functions to retain the fixed shape of the processed end 31.

In this case, the processed end 31 has a (outer) shape corresponding to the inner surface of a portion of the fitting hole (hereinafter, referred to as "tightening hole section") by which the processed end is tightened.

For example, when the fitting 28a shown in FIG. 14A is employed, where a tightening hole section of the hole has a fixed inner diameter throughout the axial length of the fitting 28, the processed end 31 has a fixed section throughout its axial length.

When the fitting 28b with the straight hole section 28d as a tightening hole section and the taper hole section 28e as shown in FIG. 18B is employed, a portion of the processed end 31 fit within the straight hole section 28d has a fixed section, whereas a portion of the processed end 31 fit within the taper hole section 28e has a convergingly tapered section.

The end of the ring fiber 29 or the processed end 31 may be snugly fitted into the fitting 28 after the shape of the slit end of the ring fiber 29 is fixed.

The fitting step where the slit end of the ring fiber 29 is snugly fit into the fitting 28 corresponds to a step of snugly fitting the processed end into the fitting for tightening.

Figure 16:
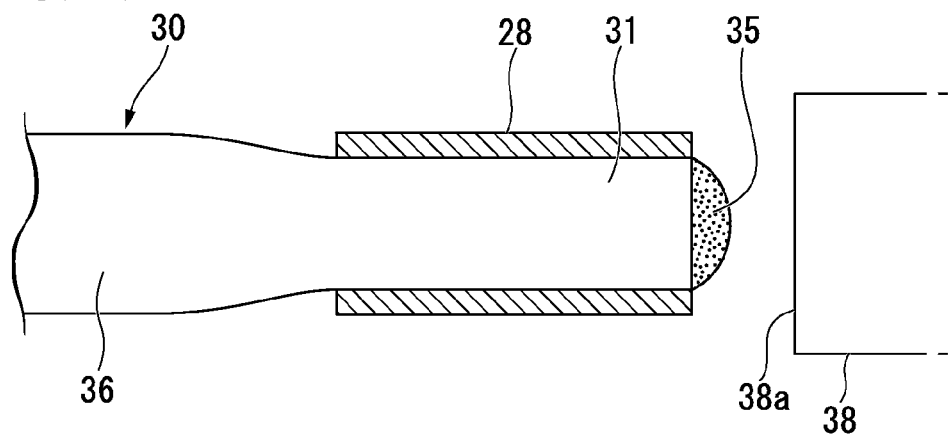
FIG. 16 is a view showing the manner in which a light entry projection extends from the processed end of the optical fiber structure.

Referring to FIG. 16, an adhesive is applied to the end face of the processed end 31 to form a dome-shaped light entry projection 35. The light entry projection 35 has an accurately convexed surface.

The adhesive has a refractive index lower than that of the bare wires 32 of the ring fiber 29 and is transparent when cured. The light entry projection 35 enhances optical coupling efficiency between the light source 38 and the processed end 31. Accordingly, the light entry projections 35 of the processed end 31 can readily increase the amount of light inputted to the optical fiber structure from the light source 38.

The light entry projection 35 is formed by depositing an adhesive such as used to fix the shape of the processed end 31.

In FIG. 16, the processed end 31 of the optical fiber structure is inserted into the fitting 28, and then, the fitting 28 and the processed end 31 are secured together with an adhesive. The light entry projection 35 may be formed by depositing an adhesive such as used to secure the fitting 28 and the processed end 31 together. The adhesive used to secure the fitting 28 and the processed end 31 together may be the same as the adhesive used to fix the shape of the processed end 31.

The fitting may be omitted. The present invention is also applicable to a structure where the fitting is omitted from the optical fiber structure shown in FIG. 16.

As mentioned above, the light source 38 is arranged at the input end 37 (processed end 31) of the optical fiber structure 30. The bare wires 32 are constructed so as to receive light from the light source 38. Thus, the optical fiber structure 30 can be used as the illumination unit 39 (see FIG. 13).

The light source 38 is arranged so that the light emitting surface 38a is oriented in a face-to-face relation to the end face of the processed end 31. Also, the center of the light emitting surface 38a is aligned with the axis of the processed end 31 of the optical fiber structure 30 so that the optical axis of light emitted from the light source 38 is substantially coincident with the axis of the processed end 31. By this arrangement, the illumination unit achieves high optical coupling efficiency between light emitted from the light source 3 and the processed end 31 and can readily increase the amount of light inputted to the input end of the optical fiber structure 30 and the amount of light outputted from the output end.

Figure 17A:
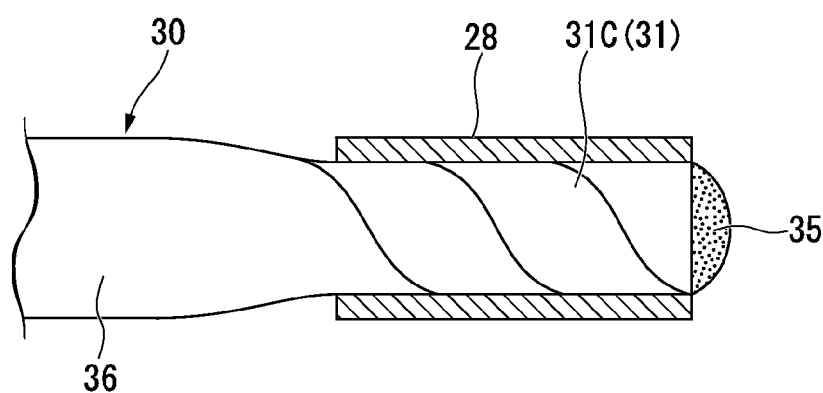
FIG. 17A is a view showing the manner in which the processed end is twisted and fit into the fitting.
Figure 17B:
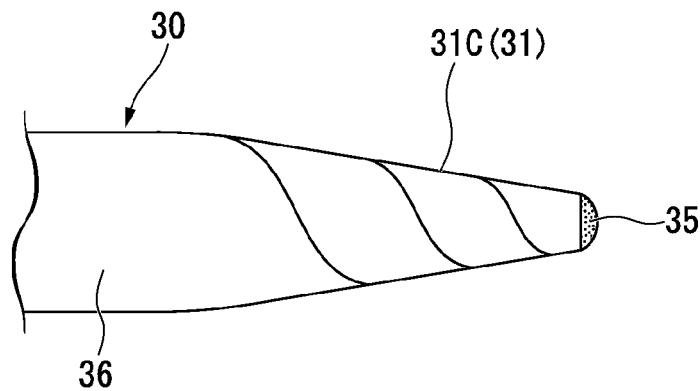
FIG. 17B is a view showing the manner in which the processed end is twisted and used in an exposed state without being inserted into a fitting.

As shown in FIGS. 17A and 17B, the processed end 31 of the optical fiber structure 30 may be twisted about the axis of the optical fiber structure 30. The processed end 31 shown in FIGS. 17A and 17B is accompanied by reference numeral 31C. The processed end 31C is formed by twisting the end of the ring fiber 29 after the cutting step is carried out to make the processed end narrower than the cylindrical section 36 of the ring fiber 29 and fixing the shape of the processed end with an adhesive. Twisting of the end of the ring fiber 29 makes it easier to narrow the processed end 31 as compared to the cylindrical section 36 of the ring fiber 29.

FIG. 17A shows that the processed end 31c is inserted into the fitting 28. FIG. 17B shows that the processed end 31C is used in an exposed condition, but not inserted into the fitting 28.

Figure 15:
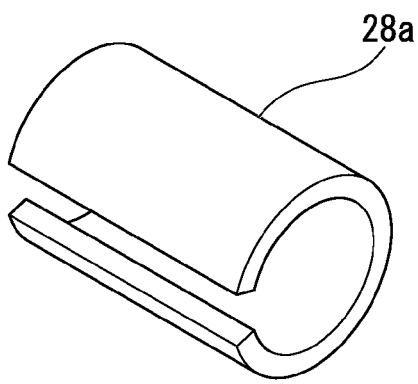
FIG. 15 is a perspective view of one example of the fitting (C-shaped fitting) shown in FIG. 14.

FIG. 17A shows the use of the C-shaped fitting 28a as used in the example shown in FIG. 15. The fitting is not limited thereto, but any of the fittings as previously mentioned in the description may be employed.

In FIGS. 17A and 17B, the light entry projection 35 extends from the end of the processed end 31C. However, the present invention is applicable to a structure where the light entry projection 35 is omitted from the processed end 31C.

Figure 18:
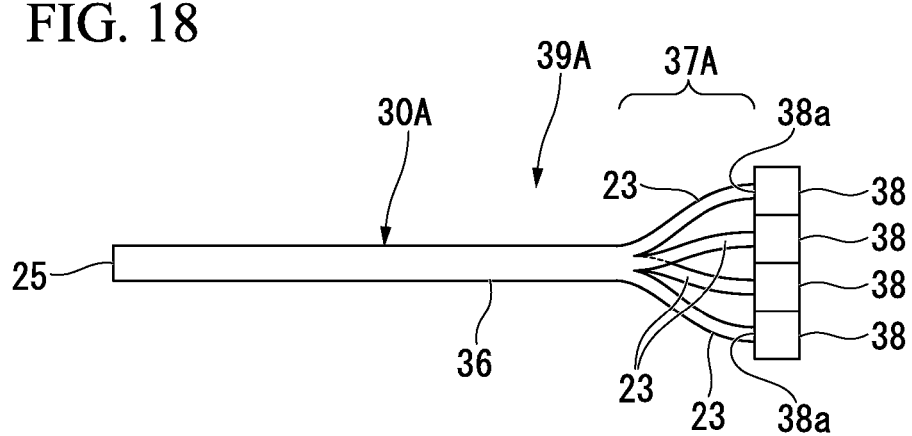
FIG. 18 illustrates a third embodiment of the present invention.

FIG. 18 shows the shape of an input end 37 of an optical fiber structure 30A made, by way of a third example, according the second embodiment of the present invention.

In the input end 37A of the optical fiber structure 30A, the end of the ring fiber 29 is circumferentially divided into a plurality of portions and arranged in a separate fashion.

The input end 37A is formed by cutting the end of the ring fiber 29 along the length of the bare wires 32, as shown, for example, in FIG. 9A, into a plurality of (illustratively, four) circumferentially discrete portions 23 (cutting step) and separating the plurality of discrete portions away from each other. The plurality of discrete portions 23 radially extend from the cylindrical section 36 of the ring fiber 29 with the tips of the discrete portions 23 separated away from each other. The end face of the bare wires 32 are exposed from each end of the end faces of the discrete portions 23.

As shown in FIG. 18, in the input end 37A, each of the discrete portions 23 may be secured to a shape fixing member provided in the input end 37A by an adhesive or the like so that the tips of the discrete portions 23 are held in a separate fashion.

As a method of fixing the tips of the plurality of discrete portions 23 of the input end 37A and holding the tips of the discrete portions 23 in a separate fashion (a discrete portions fixing method), it is not limited to a method of fixing the discrete portions 23 to the shape fixing member. For example, a molded resin section may be formed to enclose all the discrete portions 23 of the input end 37A together.

As shown in FIG. 18, a plurality of light sources 38 are provided for a plurality of corresponding discrete portions 23 in such a manner that light from the light sources 38 is inputted to the bare wires 32. This arrangement enables the optical fiber structure 30A to be used as the illumination unit 39A.

The light sources 38 have light emitting faces 38a oriented so as to face the tips of the discrete portions 23. The center of each of the light emitting face 38a is aligned with the center of the tip of the discrete portion 23.

This illumination unit thus achieves high optical coupling efficiency between light from the light sources 38 and the discrete portions 23 and thus, increases the amount of light inputted to the input end of the optical fiber structure 30A and also, the amount of light outputted from the output end.

In the optical fiber structure 30A, a dome-shaped light entry projection may be formed on the end faces of the respective discrete portions 23 by a transparent resin (adhesive and the like) in order to enhance optical coupling efficiency between output light from the light source 38 arranged so as to correspond to each of the discrete portions 23 and the bare wires 32 of the plastic optical fiber exposed from the end faces of the discrete portions 23.

The optical fiber structures used in the foregoing examples may include an image transmission unit for transmitting an image from a target portion under inspection when the input end 25 is positioned against the target portion and can be used as an endoscope and other observation devices.

In the endoscope of the present example, the image transmission unit is disposed in the cylindrical section 36 of the optical fiber structure so that light is emitted to a target portion under inspection from each of the bare wires 32 disposed around the image transmission unit. An image as captured may be transmitted to the operative side of the endoscope through the image transmission unit. As such, the endoscope of this example is preferable.

Figure 19:
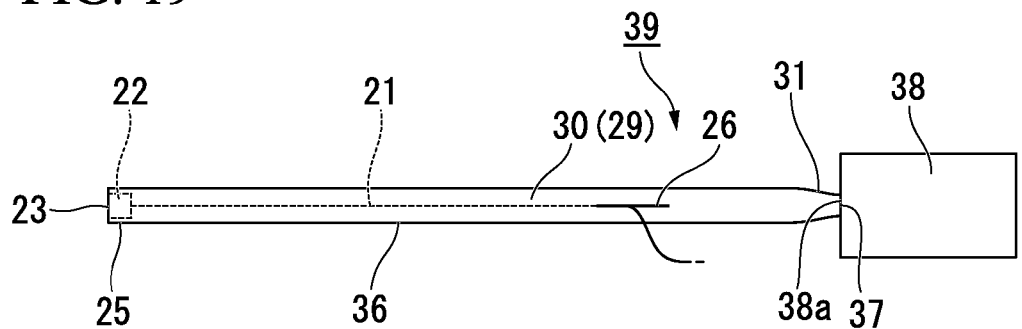
FIG. 19 is a view showing the manner in which an image capture unit and an image transmission unit (endoscope) are disposed in the optical fiber structure shown in FIGS. 8A and 8B.

FIG. 19 is an example of a configuration (an observation device) showing the manner in which an image transmission unit is disposed at the input end 25 of the optical fiber structure 30 of the illumination unit 39 illustrated in FIG. 13.

Figure 20:
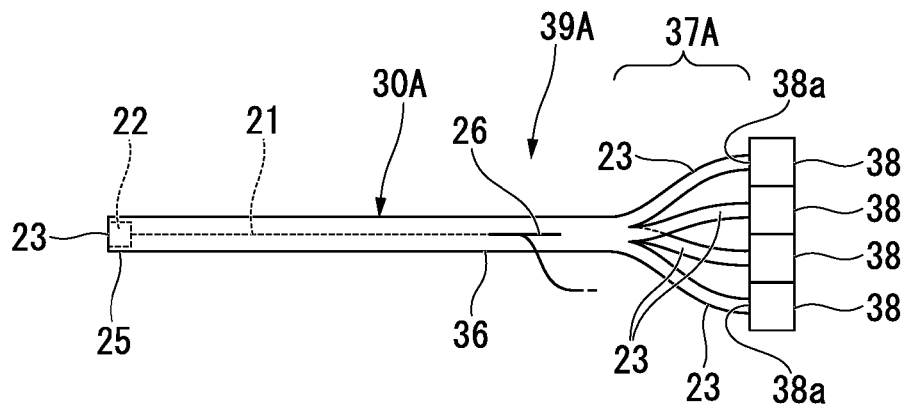
FIG. 20 is a view showing the manner in which an image capture unit and an image transmission unit (endoscope) are disposed in the optical fiber structure shown in FIG. 19.

FIG. 20 is an example of a configuration (an observation device) showing the manner in which an image transmission unit is disposed at the input end 25 of the optical fiber structure 30A of the illumination unit 39A illustrated in FIG. 18.

In FIGS. 19 and 20, the light source(s) 8 is provided at the input end 37, 37A of the optical fiber structure 30A.

In the example shown in FIGS. 19 and 20, an image capture unit 22 is mounted to the distal end of the image transmission unit 21 and has an end face 23 constructed to face against a target portion under inspection.

The endoscope and other observation devices of the present example is not limited to the specific forms, as far as the image capture unit 22 is so constructed as to capture an image of a target portion under inspection, and the image transmission unit is constructed so as to transmit the image thus captured. For example, an objective lens may be used as the image capture unit 22 where the image transmission unit 21 is an image fiber. Alternatively, when the image transmission unit 21 is an electrically conductive wire, an imaging sensor 22 such as a CCD may be disposed at the distal end of the optical fiber structure to convert the image to an electrical signal and transmit the electrical signal through the electrically conductive wire.

The optical fiber structure 30 may also be used to allow a means for injecting medicine such as in gaseous or liquid form through the hollow portion 34 (see FIG. 10), a mechanical means and the like for manipulating a target portion under inspection and other means to have access to the target portion.

In FIGS. 19 and 20, an aperture 26 is formed in the optical fiber structure 30 and located between the output end 25 and the input end 7. The linear image transmission unit 21 such as the image fiber and the electrically conductive wire is inserted through the aperture 26 into the cylindrical section 36 of the optical fiber structure 30 and extends out of the cylindrical section 36.

The aperture 26 is formed by cutting the cylindrical section 36 of the optical fiber structure 30 along the length of the bare wires 32. It is preferable to form the aperture 26 since there is a less chance of the bare wires 32 being cut. This brings about an increase in the amount of light emitted from the output end.

A preferred embodiment of the present invention has been described, but the present invention is not limited thereto. Various modifications and changes may be made without departing from the spirit of the present invention.

In the optical fiber structure of the present embodiment, the rein body 33 may be used in an exposed condition. The resin body may be surrounded by a separate jacket, tube or the like.

Also, both longitudinal ends of the optical fiber structure may form the processed ends 31. If the optical fiber structure has a processed end at its output end, the optical fiber structure can be smoothly inserted into a narrow channel.

Third Embodiment

An endoscope according to a third embodiment of the present invention will now be described with reference to FIGS. 21A to 26.

FIGS. 21A to 21C show the shape of the vicinity of an output end of an optical fiber structure 41 in first to third examples of the present invention.

The optical fiber structure 41 of the present embodiment includes a cylindrical resin body 43 and a plurality of circumferential arrays of plastic optical fiber bare wires 42 extending along the length of the resin body 43.

Figure 23:
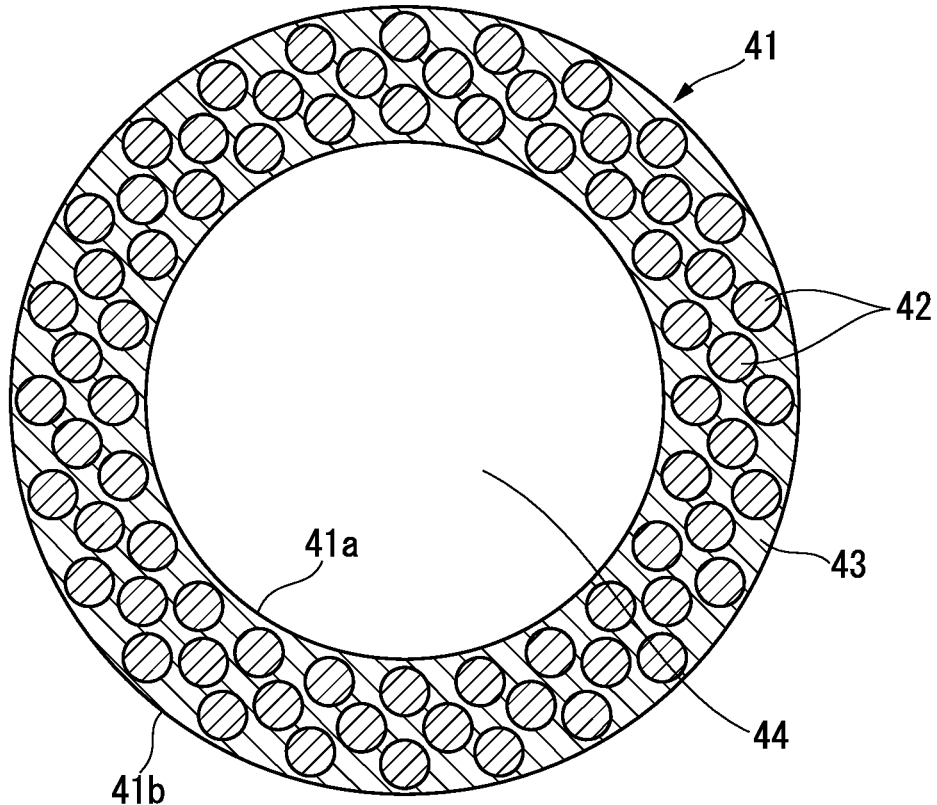
FIG. 23 is a cross-sectional view of one example of a section perpendicular to a longitudinal direction of a plastic optical fiber structure according to the present invention.

As shown in FIG. 23, the optical fiber structure 41 has a ring-shaped section. The ring-shaped resin body 43 has a hollow portion 44.

The plurality of bare wires 42 are embedded in the ring-shaped resin body 43. The bare wires 42 extend along the length of the optical fiber structure 41 (lateral direction in FIG. 1). The bare wires 42 are plastic optical fibers (POF) and each include a core surrounded by a resin sheath having a refractive index lower than that of the core. Each of the bare wires 42 utilizes the refractive index difference between the core and the sheath and functions as an optical waveguide. The core and the sheath are both made of plastic capable of transmitting light through the optical fiber structure 41.

The plastic material of which the core of the bear wire 42 is made is the same as the plastic material used in the first embodiment.

The plastic material of which the sheath of the bear wire 42 is made is the same as the plastic material used in the first embodiment.

The resin of which the resin body 43 is made is the same as the resin used in the first embodiment.

Figure 25:
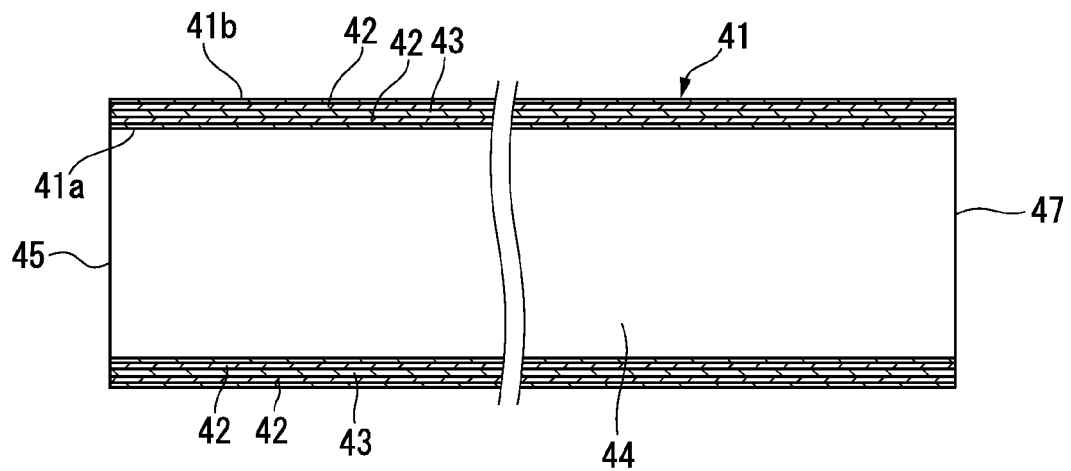
FIG. 25 is a longitudinal sectional view of one example of the optical fiber structure before the end is processed.

As shown in FIG. 25, the optical fiber structure 41 has a longitudinal input end 47 and an opposite output end 45. The bare wires 42 and the resin body 43 both extend from the input end 47 to the output end 45 along the length of the optical fiber structure 41.

The hollow portion 44 also extends along the length of the optical fiber structure 41 and is open at the opposite ends (that is, the input end 47 and the output end 45).

Figure 26:
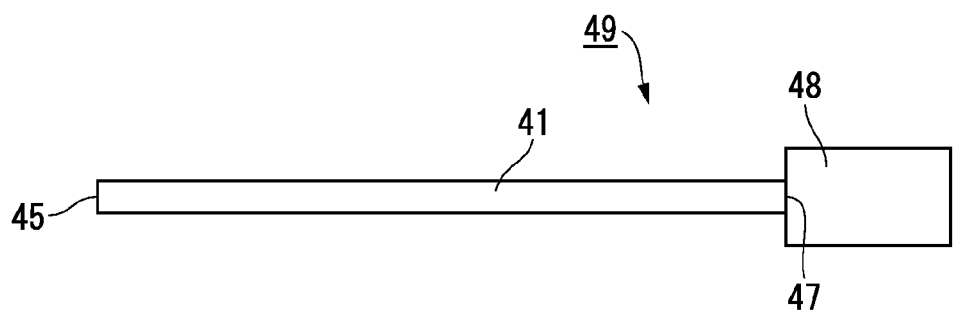
FIG. 26 is a schematic view showing the manner in which a light source is arranged at the input end of the optical fiber structure.

As shown in FIG. 26, a light source 48 is arranged at the input end 47. Light is emitted from the light source 48, is transmitted through each of the bare wires 42, and is emitted out of the output end 45.

Figure 24:
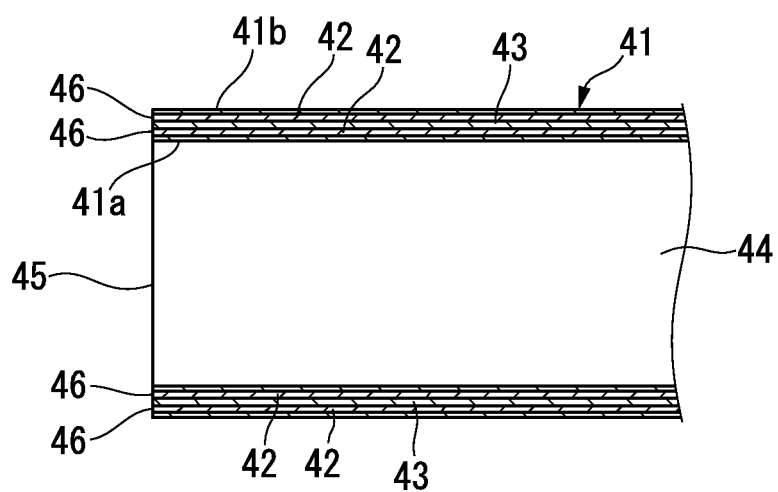
FIG. 24 is a sectional view showing one example of the vicinity of the shape of the input end of the optical fiber structure of the present invention.

As shown in FIG. 24, in a conventional plastic optical fiber structure, the output end 45 is a surface which is perpendicular to the longitudinal direction (lateral direction in FIG. 24) of the optical fiber structure. Each of the bare wires 42 has an end face 46 oriented in a direction perpendicular to the longitudinal direction of the resin body 43 such that ring-shaped illumination is obtained.

By contract, in the present invention, the end faces 46 of the plurality of bare wires 42 are inclined in at least one longitudinal end 45A, 45B, 45C of the resin body 43 of the optical fiber structure 41. By this arrangement, light as transmitted through the bare wires 42 is emitted in a direction corresponding to the angle of inclination of the end face 46 of the bare wires 42. The present invention is not limited to the specific angle of inclination. However, the angle of inclination may range from 30 to 60 degrees.

In the ends 45A, 45B, 45C, the end 46 of the bare wires 42 may be inclined as in the end face of the resin body 43. In this case, no step is formed between the end faces 46 of the bare wires 42 and the end face of the resin body 43, thereby allowing for easy processing.

The resin body 43 may have a round end face.

Referring to FIG. 21A, the end 45A of the optical fiber structure 41 is inclined so that an outer periphery 41b extends beyond an inner periphery 41a. The end 45B thus configured enables light L emitted from the plurality of bare wires 42 to be directed toward the inner periphery 41a of the optical fiber structure 41. That is, all the light is collected at the center of the optical fiber structure.

Referring to FIG. 21B, the end 45B of the optical fiber structure 41 is inclined so that the inner periphery 41a extends beyond the outer periphery 41b. The end 45A thus configured enables light L emitted from the plurality of bare wires 42 to be outwardly directed and expanded toward the outer periphery 41b of the optical fiber structure 41.

Referring to FIG. 21C, the end 45C of the optical fiber structure 41 is inclined in its entirety. The end 45C thus configured enables light L emitted from the plurality of bare wires 42 to be applied to a lateral direction substantially perpendicular (downward direction in FIG. 22C) to the longitudinal direction of the optical fiber structure 41.

In the present examples, a method of processing the ends 45A, 45B, and 45C of the optical fiber structure 41 is not limited to the specific method. The ends may be cut with such as a knife or may be abraded. Alternatively, there may be employed a mold and the like having a shape which compliments the shape of each of the ends of the optical fiber structure 41. The mold, after heated, is pressed against the end of the optical fiber structure 41. As a result, the end of the optical fiber structure 41 is thermally deformed in such a manner as to correspond to the molding surface of the mold.

As the optical fiber structure 41 is made of plastic, it can readily be processed using a knife. The use of the thermal deformation is preferable since it produces no debris.

As described above, the optical fiber structure 41 of the present invention can be used as an illumination unit if the light source 48 is provided at the input end 47. A method of optically coupling between the input end 47 and the light source 48 is not limited to the specific method. The input end 47 may be processed in such a manner that light from the light source 48 is inputted to the bare wires 42 at the input end 47. The input end 47 may not even be processed as far as light is inputted to the bare wires 42.

In the optical fiber structure 41, the end faces 46 of the both ends of the bare wires 42 may be inclined. In this case, either end can be used as an output end. If a plastic optical fiber structure has opposite ends of different shape, then there is no need to provide two plastic optical fiber structures. One of the ends may be selectively used as an output end. For example, one end may be so shaped as to collect light as in the end 45A shown in FIG. 21A, whereas the other end may be so shaped as to diffuse light as in the end 45B shown in FIG. 21B. One of the ends may be selectively used as an output end, depending on the intended use.

The optical fiber structure of the present examples may be provided with the image transmission unit to transmit an image when the output end 45 is positioned against a target portion under inspection. The optical fiber structure can thus be used as an endoscope and other observation devices. To use the optical fiber structure 41 as the illumination unit 49, the light source 48 may be arranged at the input end 47, as mentioned above.

In the present examples, the optical fiber structure 41 has the hollow portion 44, and the end faces 46 of the bare wires 42 are disposed at the output end 45 and extend around the hollow portion 44. The image transmission unit is disposed within the optical fiber structure 41. The bare wires 42 are disposed around the image transmission unit and emanate light to illuminate a target portion under inspection. An image as captured is transmitted to the operative end of the endoscope by the image transmission unit. The use of this endoscope is therefore preferred.

Figure 22A:
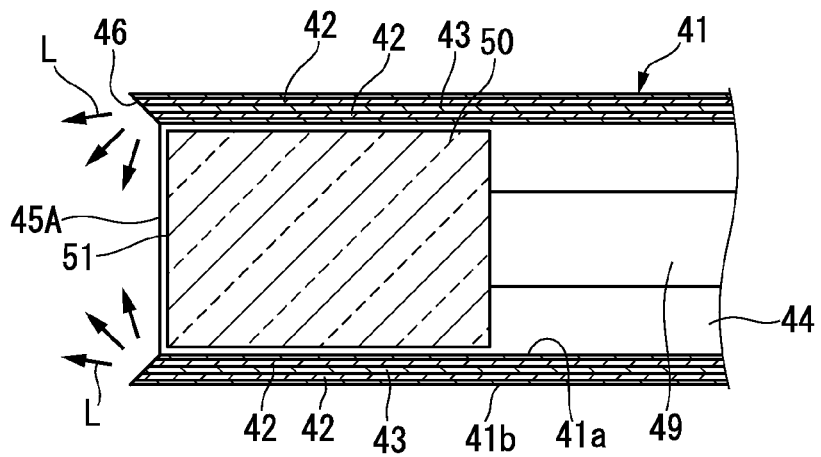
FIG. 22A is a longitudinal sectional view of the first example of the optical fiber structure according to the third embodiment of the present invention, with the distal end of an image transmission unit is arranged in the output end.
Figure 22B:
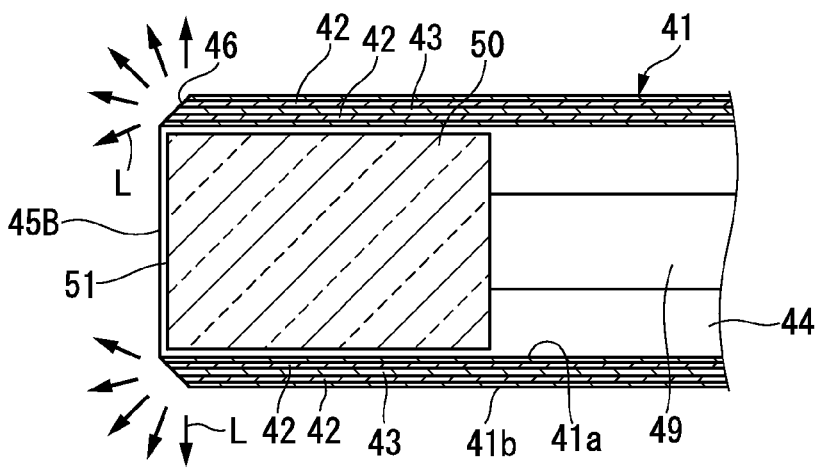
FIG. 22B is a longitudinal sectional view of the second example of the optical fiber structure according to the third embodiment of the present invention, with the distal end of an image transmission unit is arranged in the output end.
Figure 22C:
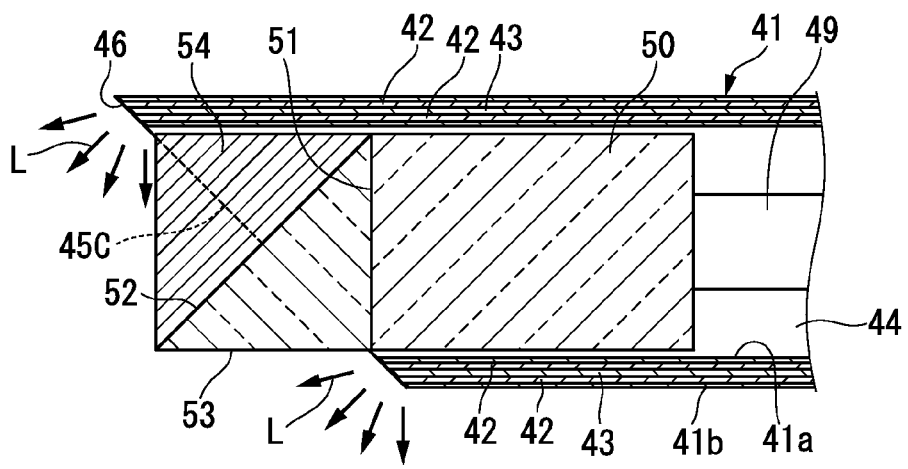
FIG. 22C is a longitudinal sectional view of a third example of the optical fiber structure according to the third embodiment of the present invention, with the distal end of an image transmission unit is arranged in the output end.

FIGS. 22A to 22C show one example of which the image transmission unit is provided at the output ends 45A, 45B, and 45C of the optical fiber structure 41 shown in FIGS. 21A to 21C.

In the examples shown in FIGS. 22A and 22B, an image capture unit 50 is disposed at the tip of an image transmission unit 49 so that an end face 51 of the image capture unit 50 can be oriented to face against a target portion under inspection.

The use of these examples is preferred when it is necessary to observe the wall of a stomach or the like located longitudinally forwardly of the optical fiber structure 41.

In FIG. 22A, the outer periphery 41b extends beyond the inner periphery 41a along the circumference of the output end 45A of the optical fiber structure 41. As such, all the lights L emanated from the plurality of bare wires 42 are collected at the center to more brightly illuminate a target portion.

In FIG. 22B, the inner periphery 41a extends beyond the outer periphery 41b along the circumference of the output end 45B of the optical fiber structure 41. As such, the lights L emanated from the plurality of bare wires 42 are outwardly directed to more widely illuminate a target portion.

In the example shown in FIG. 22C, the image transmission unit 49 is provided at its tip with the image capture unit 50. A unit 52 is mounted to the end face 51 of the image capture unit 50 so as to change the direction of observation. The unit 52 has an end face 53 extending in a direction perpendicular to the end face 51 of the image capture unit 50 and oriented to face against a target portion under inspection.

In the present embodiment, the unit for changing the direction of observation includes a prism 52. The prism 52 has a substantially triangular section and is supported by a holder 54. The prism 52 and the holder 54 are secured, for example, by an adhesive. The prism 52 and the holder 54 collectively form a substantially rectangular section so that no sharp corner is present at the front end of the prism 52.

In FIG. 22, the entire face of the output end 45C of the optical fiber structure 41 is inclined. Upon insertion of the optical fiber structure 41 into a narrow duct such as a blood vessel, it is capable of directing light L, as emanated from the plurality of bare wires 42, toward a target portion located at lateral side of the optical fiber structure 41 and observing the inner surface of the duct.

This example is preferable when observing a lateral direction with respect to a longitudinal direction of the optical fiber structure 41 (so called, "sideward viewing"), for example, the wall of a blood vessel and the like.

The endoscope and other observation devices of the present example is not limited to the specific forms, as far as the image capture unit 50 is so constructed as to capture an image of a target portion under inspection, and the image transmission unit 49 is so constructed as to transmit the image. For example, an objective lens may be used as the image capture unit 50 where the image transmission unit 49 is an image fiber. Alternatively, where the image transmission unit 49 is an electrically conductive wire, a CCD or similar imaging sensor 50 may be disposed at the distal end of the optical fiber structure to convert the image to an electrical signal and transmit the electrical signal through the electrically conductive wire.

The optical fiber structure 41 may also be used to allow a means for injecting medicine such as in gaseous or liquid form through the hollow portion 44, a mechanical means and the like for manipulating a target portion under inspection and other means to have access to the target portion.

Although a preferred embodiment of the present invention has been described, the present invention is not limited to the foregoing examples. Various medications and changes may be made without departing from the spirit of the present invention.

The optical fiber structure 41 of the present invention can be left exposed to the external surroundings during use. As an alternative, the optical fiber structure 41 may be surrounded by a separate jacket, tube or the like.

The input end of the optical fiber structure may diverge from its distal end (or output end of the optical fiber structure) in a tapered manner. The input end is hereinafter referred to as "tapered input end". The tapered input end may be circumferentially separated by at least on one or more slit. Also, the tapered input end may not have a slit.

The maximum outer diameter of the tapered input end, that is, the outer diameter of the input end of the optical fiber structure is in the order, for example, of approximately 100 mm. However, it is not limited to thereto and may have any suitable diameter.

What is claimed is:

1. An optical fiber structure comprising:
   a cylindrical resin body, the resin body comprising:
   a plurality of circumferential arrays of optical fiber bare wires which are disposed within the entire resin body and which extend along a longitudinal direction of the resin body; and
   a linear slit which extends parallel to the optical fiber bare wires from an intermediate location in a length of the resin body and extends in a radial direction from an outer surface to an inner bore of the resin body;
   wherein the resin body comprises a plurality of the slits arranged at regular intervals in a circumferential direction, and elongated portions each sandwiched between two adjacent slits in the resin body, the elongated portions being overlapped such that the resin body has a narrower outer circumference;
   wherein the elongated portions comprise a first elongated portion, and second elongated portion, and a third elongated portion, wherein the first elongated portion is disposed between the second elongated portion and the third elongated portion; and wherein the first elongated portion comprises a first section disposed at an inner surface of the second elongated portion and a second section disposed at an outer surface of the third elongated portion.

2. The optical fiber structure according to claim 1, wherein a plurality of the slits are provided in the resin body at opposed positions as viewed from the longitudinal direction of the resin body, and a plurality of elongated portions, each sandwiched between adjacent slits, are deformed to a flat shape as viewed from the longitudinal direction of the resin body.

3. An illumination unit comprising the optical fiber structure according to claim 1, and a light source arranged at one end of the optical fiber structure.

4. An endoscope comprising the optical fiber structure according to claim 1, wherein an image transmission unit which transmits an image of a target portion under inspection is disposed in an inner bore of the resin body so as to face an end portion of the optical fiber structure.

5. The endoscope according to claim 4, wherein the image transmission unit transmits the image captured by an imaging sensor.

6. The endoscope according to claim 4, wherein the image transmission unit is an image fiber.

7. The endoscope according to claim 4, wherein the image transmission unit is inserted through the slit provided at the intermediate location along the length of the resin body.

8. An optical fiber structure comprising a ring fiber, the ring fiber comprising:
a cylindrical resin body which comprises a plurality of circumferential arrays of optical fiber bare wires which are disposed within the entire resin body and which extend in a longitudinal direction of the resin body; and
a processed end formed by cutting at least one longitudinal end of the ring fiber along a longitudinal direction of the bare wires and overlapping separated portions in a circumferential direction of the ring fiber so that the processed end is narrower than a cylindrical section of the ring fiber;
wherein the resin body comprises a plurality of the slits arranged at regular intervals in a circumferential direction, and elongated portions each sandwiched between two adjacent slits in the resin body, the elongated portions being overlapped such that the resin body has a narrower outer circumference;
wherein the elongated portions comprise a first elongated portion, and second elongated portion, and a third elongated portion, wherein the first elongated portion is disposed between the second elongated portion and the third elongated portion; and
wherein the first elongated portion comprises a first section disposed at an inner surface of the second elongated portion and a second section disposed at an outer surface of the third elongated portion.

9. The optical fiber structure according to claim 8, further comprising a fitting, wherein the processed end is inserted into the fitting which tightens the processed end.

10. The optical fiber structure according to claim 8, wherein the processed end is further formed by twisting the at least one longitudinal end of the ring fiber.

11. The optical fiber structure according to claim 8, further comprising a light entry projection formed at a tip of the processed end, the light entry projection comprising a curved convex surface comprising a transparent adhesive with a refractive index lower than a refractive index of the bare wires.

12. The optical fiber structure according to claim 8, wherein the processed end comprises a plurality of discrete portions collected together, the plurality of discrete portions dividedly formed during the cutting of the at least one longitudinal end of the ring fiber.

13. The optical fiber structure according to claim 9, wherein the fitting comprises a taper hole.

14. A method of manufacturing an optical fiber structure comprising a ring fiber comprising a cylindrical resin body which comprises a plurality of circumferential arrays of optical fiber bare wires which are disposed within the entire resin body and which extend along a longitudinal direction of the resin body,
wherein the resin body comprises a plurality of the slits arranged at regular intervals in a circumferential direction, and elongated portions each sandwiched between two adjacent slits in the resin body, the elongated portions being overlapped such that the resin body has a narrower outer circumference,
wherein the elongated portions comprise a first elongated portion, and second elongated portion, and a third elongated portion, wherein the first elongated portion is disposed between the second elongated portion and the third elongated portion, and
wherein the first elongated portion comprises a first section disposed at an inner surface of the second elongated portion and a second section disposed at an outer surface of the third elongated portion,
the method comprising:
cutting at least one longitudinal end of the ring fiber along a longitudinal direction of the bare wires;
overlapping separated portions, of the at least one longitudinal end, in a circumferential direction of the ring fiber; and
forming a processed end from the at least one longitudinal end such that the processed end is narrower than a cylindrical section of the ring fiber.

15. The method of manufacturing an optical fiber structure according to claim 14, further comprising inserting the at least one longitudinal end, subjected to the cutting, into a fitting, thereby tightening the at least one longitudinal end.

16. The method of manufacturing an optical fiber structure according to claim 14, further comprising twisting the at least one longitudinal end, subjected to the cutting.

17. The method of manufacturing an optical fiber structure according to claim 14, further comprising forming a light entry projection, comprising a curved convex surface at a tip of the processed end, by using transparent adhesive with a refractive index lower than a refractive index of the bare wires.

18. The method of manufacturing an optical fiber structure according to claim 14, further comprising collecting the separated portions dividedly formed during the cutting.

19. An optical fiber structure comprising a ring fiber, the ring fiber comprising:
a cylindrical resin body which comprises a plurality of circumferential arrays of optical fiber bare wires which are disposed within the entire resin body and which extend in a longitudinal direction of the resin body; and
a plurality of discrete portions formed by cutting at least one longitudinal end of the ring fiber along the longitudinal direction of the bare wires, the discrete portions being separated away from each other;

wherein the resin body comprises a plurality of the slits arranged at regular intervals in a circumferential direction, and elongated portions each sandwiched between two adjacent slits in the resin body, the elongated portions being overlapped such that the resin body has a narrower outer circumference;

wherein the elongated portions comprise a first elongated portion, and second elongated portion, and a third elongated portion, wherein the first elongated portion is disposed between the second elongated portion and the third elongated portion; and wherein the first elongated portion comprises a first section disposed at an inner surface of the second elongated portion and a second section disposed at an outer surface of the third elongated portion.

20. A method of manufacturing an optical fiber structure comprising a ring fiber, the ring fiber comprising a cylindrical resin body which comprises a plurality of circumferential arrays of optical fiber bare wires which are disposed within the entire resin body and which extend in a longitudinal direction of the resin body, wherein the resin body comprises a plurality of the slits arranged at regular intervals in a circumferential direction, and elongated portions each sandwiched between two adjacent slits in the resin body, the elongated portions being overlapped such that the resin body has a narrower outer circumference, wherein the elongated portions comprise a first elongated portion, and second elongated portion, and a third elongated portion, wherein the first elongated portion is disposed between the second elongated portion and the third elongated portion, and wherein the first elongated portion comprises a first section disposed at an inner surface of the second elongated portion and a second section disposed at an outer surface of the third elongated portion, the method comprising:

cutting at least one longitudinal end of the ring fiber along a longitudinal direction of the bare wires and thereby forming a plurality of discrete portions; and separating the discrete portions away from each other.

21. An illumination unit comprising the optical fiber structure according to claim 19, further comprising a plurality of light sources arranged at an input end of the optical fiber structure so that the light sources respectively correspond to the discrete portions.

22. An optical fiber structure comprising a cylindrical resin body, the resin body comprising:

a plurality of circumferential arrays of optical fiber bare wires which are disposed within the entire resin body and which extend in a longitudinal direction of the resin body; and at least one longitudinal end, wherein each of the bare wires comprises an inclined end face at the end of the resin body;

wherein the resin body comprises a plurality of the slits arranged at regular intervals in a circumferential direction, and elongated portions each sandwiched between two adjacent slits in the resin body, the elongated portions being overlapped such that the resin body has a narrower outer circumference;

wherein the elongated portions comprise a first elongated portion, and second elongated portion, and a third elongated portion, wherein the first elongated portion is disposed between the second elongated portion and the third elongated portion; and wherein the first elongated portion comprises a first section disposed at an inner surface of the second elongated portion and a second section disposed at an outer surface of the third elongated portion.

23. The optical fiber structure according to claim 22, wherein at the end, the end faces of the bare wires are inclined together with an end face of the resin body around the end faces of the bare wires.

24. The optical fiber structure according to claim 22, wherein an output end of the optical fiber structure comprises an outer periphery and an inner periphery, and the outer periphery is shaped to project beyond the inner periphery along an entire circumference of the output end.

25. The optical fiber structure according to claim 22, wherein an output end of the optical fiber structure comprises an outer periphery and an inner periphery, and the inner periphery is shaped to project beyond the outer periphery along an entire circumference of the output end.

26. The optical fiber structure according to claim 23, wherein an output end of the optical fiber structure in its entirety is inclined along a single plane.

27. An illumination unit comprising the optical fiber structure according to claim 8, and a light source arranged at the input end of the optical fiber structure.

28. An illumination unit comprising the optical fiber structure according to claim 22, and a light source arranged at the input end of the optical fiber structure.

29. An endoscope comprising the optical fiber structure according to claim 8, and an image transmission unit disposed within the optical fiber structure, wherein the image transmission unit transmits an image of a target portion under inspection that opposes an output end face.

30. An endoscope comprising the optical fiber structure according to claim 19, further comprising an image transmission unit disposed within the optical fiber structure, wherein the image transmission unit transmits an image of a target portion under inspection that opposes an output end face.

31. An endoscope comprising the optical fiber structure according to claim 22, further comprising an image transmission unit disposed within the optical fiber structure, wherein the image transmission unit transmits an image of a target portion under inspection that opposes an output end face.

32. The endoscope according to claim 29, further comprising an imaging sensor provided at a distal end of the image transmission unit.

33. The endoscope according to claim 30, further comprising an imaging sensor provided at a distal end of the image transmission unit.

34. The endoscope according to claim 31, further comprising an imaging sensor provided at a distal end of the image transmission unit.

35. The endoscope according to claim 29, wherein the image transmission unit is an image fiber.

36. The endoscope according to claim 30, wherein the image transmission unit is an image fiber.

37. The endoscope according to claim 31, wherein the image transmission unit is an image fiber.

* * * * *